United States Patent
Silberstein et al.

(10) Patent No.: US 10,064,881 B2
(45) Date of Patent: Sep. 4, 2018

(54) NATURAL FORMULATIONS

(75) Inventors: Tova Silberstein, Jerusalem (IL); Rachel Lutz, Alon-Shvut (IL); Shlomo Magdassi, Jerusalem (IL); Barak Tzadok, Jerusalem (IL)

(73) Assignees: Y&B Mother's Choice Ltd., Jerusalem (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 349 days.

(21) Appl. No.: 13/992,309

(22) PCT Filed: Dec. 8, 2011

(86) PCT No.: PCT/IL2011/050054
§ 371 (c)(1),
(2), (4) Date: Jun. 7, 2013

(87) PCT Pub. No.: WO2012/077120
PCT Pub. Date: Jun. 14, 2012

(65) Prior Publication Data
US 2013/0287708 A1   Oct. 31, 2013

Related U.S. Application Data

(60) Provisional application No. 61/421,467, filed on Dec. 9, 2010, provisional application No. 61/422,191, filed on Dec. 12, 2010.

(51) Int. Cl.
| | |
|---|---|
| A61K 31/70 | (2006.01) |
| A61K 45/06 | (2006.01) |
| A61K 8/92 | (2006.01) |
| A61K 8/44 | (2006.01) |
| A61K 8/98 | (2006.01) |
| A61Q 5/02 | (2006.01) |
| A61Q 19/00 | (2006.01) |
| A61K 8/64 | (2006.01) |
| A61K 8/55 | (2006.01) |
| A61K 8/34 | (2006.01) |
| A61K 8/63 | (2006.01) |
| A61K 8/73 | (2006.01) |
| A61K 8/97 | (2017.01) |
| A61K 36/00 | (2006.01) |
| A61Q 11/00 | (2006.01) |

(52) U.S. Cl.
CPC .............. *A61K 31/70* (2013.01); *A61K 8/345* (2013.01); *A61K 8/44* (2013.01); *A61K 8/553* (2013.01); *A61K 8/63* (2013.01); *A61K 8/64* (2013.01); *A61K 8/73* (2013.01); *A61K 8/737* (2013.01); *A61K 8/922* (2013.01); *A61K 8/97* (2013.01); *A61K 8/988* (2013.01); *A61K 36/00* (2013.01); *A61K 45/06* (2013.01); *A61Q 5/02* (2013.01); *A61Q 19/00* (2013.01); *A61K 2236/30* (2013.01); *A61Q 11/00* (2013.01)

(58) Field of Classification Search
CPC ........ A61K 31/70; A61K 45/06; A61K 8/922; A61K 8/97; A61K 8/44; A61K 36/00; A61K 8/988; A61K 8/345; A61K 8/737; A61K 8/73; A61K 8/64; A61K 8/63; A61K 8/553; A61K 2236/30; A61Q 5/02; A61Q 19/00; A61Q 11/00
See application file for complete search history.

(56) References Cited

U.S. PATENT DOCUMENTS

| | | | |
|---|---|---|---|
| 2,996,540 | A | 8/1967 | Pearl |
| 4,247,569 | A | 1/1981 | Hata et al. |
| 4,511,555 | A | 4/1985 | Faust |
| 5,080,901 | A | 1/1992 | Hangay et al. |
| 5,397,778 | A | 3/1995 | Forse et al. |
| 5,455,232 | A | 10/1995 | Piljac et al. |
| 5,466,675 | A | 11/1995 | Piljac et al. |
| 5,503,766 | A | 4/1996 | Kulperger |
| 5,514,661 | A | 5/1996 | Piljac et al. |
| 5,639,794 | A | 6/1997 | Emerson et al. |
| 5,817,314 | A | 10/1998 | So et al. |
| 6,475,476 | B1 | 11/2002 | Fluker |
| 6,485,711 | B1 | 11/2002 | Olmstead |
| 6,548,463 | B2 | 4/2003 | Miyahara et al. |
| 7,001,877 | B1 | 2/2006 | Grier |
| 7,129,218 | B2 | 10/2006 | Stipcevic et al. |
| 7,262,171 | B1 | 8/2007 | Piljac et al. |
| 2006/0003022 | A1 | 1/2006 | McNeff et al. |
| 2006/0018867 | A1 | 1/2006 | Kawasaki et al. |
| 2006/0143838 | A1* | 7/2006 | Palpu ............ A61K 8/97 8/405 |
| 2007/0202062 | A1* | 8/2007 | Workman ......... A61Q 5/02 424/66 |

(Continued)

FOREIGN PATENT DOCUMENTS

| | | |
|---|---|---|
| AU | 747088 | 5/2002 |
| CA | 2 460 825 A1 | 9/2005 |

(Continued)

OTHER PUBLICATIONS

Chen et al., "Chemical constituents in Populus davidiana", Chinese Traditional and Herbal Drugs, vol. 37, No. 6, pp. 816-818, (2006). English Abstract on p. 816.

Lin, "The flavour component and antimicrobiol insecticidal functiond of Wasabi", China Condiment, vol. 1, No. 1, pp. 12-14 and 23, (2004). English Abstract on p. 12.

Tang et al., "Bioactivities and Application Research of Saponin from Pericarps of Sapindus mukorossi", Nat Prod Res Dev, vol. 19, pp. 562-565, (2007). English Abstract on p. 562.

Zhao et al., "Study on honeysuckle antimicrobial extraction and antimicrobial effect", Journal of Shaoyang College, vol. 14, No. 3, pp. 204-209, (2001). English Abstract on p. 209.

(Continued)

*Primary Examiner* — Snigdha Maewall
(74) *Attorney, Agent, or Firm* — Vorys, Sater, Seymour and Pease LLP

(57) ABSTRACT

Provided is an all natural composition including naturally-obtained plant extracts.

11 Claims, No Drawings

(56) References Cited

U.S. PATENT DOCUMENTS

| | | | |
|---|---|---|---|
| 2007/0231403 A1* | 10/2007 | Park | A61K 36/14 424/539 |
| 2010/0183528 A1 | 7/2010 | Maloney et al. | |
| 2011/0020302 A1 | 1/2011 | Banov et al. | |
| 2011/0052514 A1* | 3/2011 | Justen | A61K 8/0212 424/59 |
| 2012/0129950 A1* | 5/2012 | Macinga | A01N 31/02 514/738 |

FOREIGN PATENT DOCUMENTS

| | | |
|---|---|---|
| CA | 2 195 419 C | 1/2008 |
| CA | 2 129 542 C | 4/2008 |
| CA | 2 378 557 C | 12/2009 |
| CA | 2 321 926 C | 4/2010 |
| CA | 2 658 873 A1 | 9/2010 |
| CN | 1056525 A | 11/1991 |
| CN | 1096918 A | 1/1995 |
| CN | 1240640 A | 1/2000 |
| CN | 1344537 A | 4/2002 |
| CN | 1349792 A | 5/2002 |
| CN | 1370515 A | 9/2002 |
| CN | 101214208 A | 7/2008 |
| CN | 101390816 A | 3/2009 |
| CN | 101554369 A | 10/2009 |
| CN | 101732208 A | 6/2010 |
| CN | 101978844 A | 2/2011 |
| CN | 102028640 A | 4/2011 |
| CN | 102247309 A | 11/2011 |
| CN | 102379836 A | 3/2012 |
| CN | 103598225 B | 7/2015 |
| EP | 1 053 782 A1 | 11/2000 |
| EP | 1 287 742 A1 | 3/2003 |
| EP | 1 889 623 A2 | 2/2008 |
| ES | 2 259 933 A1 | 10/2006 |
| FR | 2 730 634 A1 | 8/1996 |
| FR | 2 924 123 A1 | 5/2009 |
| JP | 52-125510 A | 10/1977 |
| JP | 60-38317 A | 2/1985 |
| JP | 64-68307 A | 3/1989 |
| JP | 6-57298 A | 3/1994 |
| JP | 9-503196 A | 3/1997 |
| JP | 9-249577 A | 9/1997 |
| JP | 10-502925 A | 3/1998 |
| JP | 10-298595 A | 11/1998 |
| JP | 2000-191513 A | 7/2000 |
| JP | 2001322943 A | 11/2001 |
| JP | 2002000447 A | 1/2002 |
| JP | 2002-265327 A | 9/2002 |
| JP | 2002265327 * | 9/2002 |
| JP | 2002-363065 A | 12/2002 |
| JP | 2003096489 A | 4/2003 |
| JP | 2003-267834 A | 9/2003 |
| JP | 2004-631 A | 1/2004 |
| JP | 2004-331961 A | 11/2004 |
| JP | 2005289912 * | 10/2005 |
| JP | 2005343883 A | 12/2005 |
| JP | 3860206 B2 | 12/2006 |
| JP | 2007-223905 A | 9/2007 |
| JP | 2008-120745 A | 5/2008 |
| JP | 2008120745 A * | 5/2008 |
| JP | 2009007266 A | 1/2009 |
| JP | 2012-077037 A | 4/2012 |
| KR | 10-0821842 B1 | 4/2008 |
| KR | 10-0821846 B1 | 4/2008 |
| KR | 2010-0077554 A | 7/2010 |
| RO | 110679 * | 3/1996 |
| RO | 110679 B1 | 3/1996 |
| RU | 2 124 899 C1 | 1/1999 |
| RU | 2 126 687 C1 | 2/1999 |
| RU | 2 154 480 C1 | 8/2000 |
| RU | 2 162 701 C1 | 2/2001 |
| RU | 2 179 978 C1 | 2/2002 |
| RU | 2 210 379 C1 | 8/2003 |
| RU | 2 234 913 C1 | 8/2004 |
| RU | 2 247 571 C2 | 3/2005 |
| RU | 2 328 301 C2 | 7/2008 |
| RU | 2328301 C2 * | 7/2008 |
| TW | 200944244 A | 11/2009 |
| WO | 93/14767 A2 | 8/1993 |
| WO | 96/41528 A1 | 12/1996 |
| WO | 98/48768 A1 | 11/1998 |
| WO | 99/43334 A1 | 9/1999 |
| WO | 00/72861 A1 | 12/2000 |
| WO | 01/10447 A1 | 2/2001 |
| WO | 02/092823 A1 | 11/2002 |
| WO | 03/097003 A1 | 11/2003 |
| WO | 2005/099729 A2 | 10/2005 |
| WO | 2006/007741 A1 | 1/2006 |
| WO | 2008/013899 A2 | 1/2008 |
| WO | 2009/153800 A1 | 12/2009 |
| WO | 2012/077119 A2 | 6/2012 |
| WO | 2012/077120 A2 | 6/2012 |

OTHER PUBLICATIONS

Chen et al., "Chemical constituents in Populus davidiana", Chinese Traditional and Herbal Drugs, vol. 37, No. 6, pp. 816-818, (2006), Full English Translation.
Lin, "The flavour component and antimicrobiol insecticidal functiond of Wasabi", China Condiment, vol. 1, No. 1, pp. 12-14 and 23, (2004), Full English Translation.
Tang et al., "Bioactivities and Application Research of Saponin from Pericarps of Sapindus mukorossi", Nat Prod Res Dev, vol. 19, pp. 562-565, (2007), Full English Translation.
Zhao et al., "Study on honeysuckle antimicrobial extraction and antimicrobial effect", Journal of Shaoyang College, vol. 14, No. 3, pp. 204-209, (2001), Full English Translation.
Shiau, et al., "Quantification from Saponin from a Soapberry (Sapindus mukorossi Gaertn) in Cleaning Products by a Chromatographic and two Colorimetric Assays", J. Fac. Agr., Kyushi Univ., vol. 54, No. 1, pp. 215-221, (2009).
Natural Preservative—Aspen Bark Extract, online at http://www.theherbarie.com/Aspen-Bark-Extract-pr-463.html, four pages, retrieved online Jun. 10, 2013.
Natural Soap Recipe, online at http://www.essortment.com/natural-soap-recipe-38714.html, three pages, retrieved online Jun. 10, 2013.
Osbourn, et al., "The saponins—polar isoprenoids with important and diverse biological activities", Nat. Prod. Rep., vol. 28, pp. 1261-1268, (2011).
Saha, et al., "Structure-biological activity relationships in triterpenic saponins: the relative activity of protobassic acid and its derivatives against plant pathogenic fungi", Pest Manag Sci, vol. 66, pp. 825-831, (2010).
Huang, et al., "Triterpenoid saponins from the fruits and galls of Sapindus mukorossi", Phytochemistry, vol. 69, pp. 1609-1616, (2008).
Sea Kelp Moisturizer (high performance anti-aging moisturizer); online at http://www.benaturalorganics.com/details-sea-kelp-moisturizer.html, two pages, retrieved online Jun. 10, 2013.
Murgu, et al., "Dereplication of Glycosides from Sapindus saponaria using Liquid Chromatography—Mass Spectrometry", J. Braz. Chem. Soc., vol. 17, No. 7, pp. 1281-1290, (2006).
International Search Report for International Application No. PCT/IL2011/050053, three pages, dated Nov. 27, 2012.
The International Search Report for International Application No. PCT/IL2011/050054, four pages, dated Mar. 1, 2013.
Shin et al., "Bactericidal activity of wasabi (Wasabia japonica) against Helicobacter pylori", 94 (2004) 255-261.
Aneja et al., "in Vitro Antimicrobial Actitvity of Sapindus mukorossi and Emblica othcinalis Against Dental Caries Pathogens", Ethnobotanical Leaflets, 14: 402-412, 2010. Jan. 4, 2010.
Silici et al., "Chemical compostion and antibacterial activity of propolis collected by three different races of honeybees in the same region", 99 (2005) 69-73.
Abeytunga et al., "Structure-Antibacterial Activity Relationship of Some Aromatic Acids", J. Natn. Sci. Coun. Sri Lanka, vol. 26, No. 2, pp. 133-139, (1998).

(56) References Cited

OTHER PUBLICATIONS

Guzman, "Natural Cinnamic Acids, Synthetic Derivatives and Hybrids with Antimicrobial Activity", Molecules, vol. 19, pp. 19292-19349, (2014).

Li et al., "Analysis and evaluation of essential oil components of cinnamon barks using GC-MS and FTIR spectroscopy", Industrial Crops and Products, vol. 41, pp. 269-278, (2013).

Paranagama et al., "A Comparison of Essential Oil Constituents of Bark, Leaf, Root and Fruit of Cinnamon (*Cinnamomum zeylanicum* Blum) Grown in Sri Lanka", J. Natn. Sci. Foundation Sri Lanka, vol. 29, Nos. 3 & 4, pp. 147-153, (2001).

Pastarova et al., "Analytical Study of Free and Ester Bound Benzoic and Cinnamic Acids of Gum Benzoin Resins by GC-MS and HPLC-frit FAB-MS", Phytochemical Analysis, vol. 8, pp. 63-73, (1997).

Pundir et al., "Evaluation of five chemical food preservatives for their antibacterial activity against bacterial isolates from bakery products and mango pickles", J. Chem. Pharm. Res., vol. 3, No. 1, pp. 24-31, (2011).

\* cited by examiner

NATURAL FORMULATIONS

FIELD OF THE INVENTION

This invention generally relates to all-natural formulations for a variety of applications.

BACKGROUND OF THE INVENTION

Recent studies conducted by the U.S. environmental protection agency (EPA) revealed that human blood and lipid tissues contain up to 400 hazards chemicals originating from cosmetics and food products. Those chemicals may bring about various cancers and various chronic disorders.

Such studies have encouraged the development of "all-natural" cosmetic compositions; however, to date, none of the available compositions, particularly those regarded as body soaps/shampoos, are 100% natural. Several of the products known today contain mainly synthetic ingredients, with only a very small amount of natural ingredients. Other products contain a higher percentage of natural ingredients, with some synthetic materials, mainly synthetic stabilizers and preservatives.

U.S. Pat. No. 4,511,555 [1] discloses herbal hair treatment compositions, which include natural herbs; however, the main components in the examples are the synthetic surfactants monoethanolamine lauryl sulfate and ethylene glycol monostearate.

U.S. Pat. No. 5,080,901 [2] discloses cosmetic compositions containing plant extracts; however, according to the examples only a small percent of the formulations are plant extracts, while the rest of the components are synthetics.

French Patent No. FR2730634 [3] discloses a formulation containing one plant extract together with synthetic materials.

Similarly, U.S. Pat. No. 6,475,476 [4] discloses compositions containing herbs together with synthetic soap ingredients.

REFERENCES

[1] U.S. Pat. No. 4,511,555
[2] U.S. Pat. No. 5,080,901
[3] French Patent No. FR2730634
[4] U.S. Pat. No. 6,475,476

SUMMARY OF THE INVENTION

There is a long-felt need in the field of cosmetics and personal care and hygiene products for all-natural products which are devoid of the toxicity associated with many of the synthetic preservatives and other chemicals in use today.

Thus, in one aspect of the present invention, there is provided a composition comprising a naturally-obtained saponin material, at least one naturally-obtained thickening agent, at least one naturally-obtained humectant, at least one naturally-obtained preservative and at least one naturally-obtained additive.

As may be realized, the composition of the invention is an "all-natural" composition wherein each of the components contained in the composition is obtained from a natural source (plant or non-plant source, e.g., animal source) in a substantially unmodified form, namely in the form which exists in the material natural origin. The components may be obtained from their natural source by way of extraction or other ways of separation. Thus, the components of the formulations of the invention may be organic or aqueous extracts and/or minerals and electrolytes, or fermentation products.

The composition of the invention may be formulated into a variety of formulations for different purposes, particularly as personal care formulations. The formulations may contain an acceptable carrier or excipient, which is too obtained from a natural source. In some embodiments, the carrier is selected from water, pharmaceutically acceptable alcohols (e.g., ethanol) and polyols and pharmaceutically acceptable oils.

For the sake of clarity, it should be noted that the terms "composition" and "formulation" are used herein to denote products of the present invention. Each composition of the invention may be formulated into a suitable formulation based on the intended purpose.

The formulations are suitable for use on hair and skin, for delivering cosmetic or therapeutic actives to the skin for providing cleansing, moisturizing, minimizing or treating skin imperfections, reducing skin oiliness, providing fragrance to the hair or skin and further provide the benefit of reliving skin dryness and signs of aging.

The formulations of the invention are, in some embodiments, topically applied to the skin or hair. The formulations of the invention, unless otherwise specifically indicated, are aimed at providing topical non-systemic effect.

The personal care formulations may be used in a conventional manner for cleansing and conditioning the hair and/or skin. The formulations may be applied to the desired area of the skin in an amount sufficient to provide the desired effect. The application of the formulation may be directly onto the skin or indirectly via the use of an implement such as a cosmetic puff, a washcloth, a patch, a sticker, a wipe or a sponge.

The formulations can therefore be in the form of liquid, semi-liquid, foam, cream, oil-in-water emulsion, water-in-oil emulsion, lotion or gel for topical application to the hair or skin. Non-limiting examples of such formulations, used in accordance with the present invention, include shampoo, shampoo gel, a conditioning shampoo, a hair conditioner, soap, a liquid soap, a body wash, a moisturizing body wash, a moisturizing cream, hair care cream or soap, intimate wash, aerosol, a shower gel, a skin cleanser, a cleansing milk, a makeup remover, hair and body wash, in shower body moisturizer, a pet shampoo, a shaving preparation (shaving foam), toothpaste, mouthwash and deodorant.

As used herein, the "saponin material" is at least one naturally obtained saponin compound, as known in the art. When isolated from a natural source, the at least one saponin may be used in its substantially pure form (namely at least 85%, 87%, 92%, 95%, or 98% purity), or may be used as a saponin-containing extract isolated by a method known in the art or by a method of the invention, as disclosed herein.

In accordance with the present invention, the saponin-containing extract (herein referred to for the purpose of brevity as "saponin extract") contains at least between 0.2% and 95 wt % saponins, out of the total weight of the dry content of the extract. In some embodiments, the extract used in accordance with the present invention comprises between 0.2% and 99 wt % saponins out of the total weight of the dry content of the extract.

In some embodiments, the extract used in accordance with the present invention comprises between 10% and 80 wt % saponins out of the total weight of the dry content of the extract. In other embodiments, the extract used in accordance with the present invention comprises between 10% and 60 wt % saponins out of the total weight of the dry content of the extract. In further embodiments, the extract used in accordance with the present invention comprises between 10% and 50 wt % saponins out of the total weight of the dry content of the extract. In additional embodiments, the extract used in accordance with the present invention comprises between 10% and 40 wt % saponins out of the total weight of the dry content of the extract. In still additional embodiments, the extract used in accordance with the present invention comprises between 10% and 30 wt % saponins out of the total weight of the dry content of the extract.

In some embodiments, the extract used in accordance with the present invention comprises between 10% and 20 wt % saponins out of the total weight of the dry content of the extract.

In some embodiments, the extract used in accordance with the present invention comprises between 0.2% and 10 wt % saponins out of the total weight of the dry content of the extract.

The saponin-containing extract may be obtained from any natural source known to comprise saponins. Such natural source may be a plant source, some of which are detailed infra, and also from non-plant sources such as animal sources and marine organisms, such as starfish and sea cucumbers. In some embodiments of the invention, the saponins are extracted from a plant source, naturally grown or genetically modified to have high saponin content.

In some embodiments of the invention, the saponin material is obtained by extraction from a plant source by employing water, alcohol or a water/alcohol solution. In some embodiments, the alcohol is ethanol or methanol.

In some embodiments, the extraction is achieved by employing a water/alcohol solution. In some embodiments, the water/alcohol solution has a water:alcohol ratio of between 80:20 to 20:80. In further embodiments, the water/alcohol solution has a water:alcohol ratio of between 60:40 to 40:60. In further embodiments, the water/alcohol solution has a water:alcohol ratio of between 70:30 to 30:70. In further embodiments, the water/alcohol solution is 80:20 water/alcohol, 60:40 water/alcohol, 50:50 water/alcohol, 40:60 water/alcohol ratio, 20:80 water/alcohol, 70:30 water/ethanol or 30:70 water ethanol.

The extraction time may vary without limitation from 2 to 8 hours, at or above room temperature (20° C.-30° C.), e.g., above 30° C., 40° C., 50° C. or 60° C. In some embodiments, the extraction is carried out at a temperature between 30° C. and 70° C.

In some embodiments, the saponin material is obtained from a plant source. The plant source may be selected from shikakai, soy beans, beans, peas (*Pisum sativum*), lucerne, tea, spinach, sugar beet, quinoa, liquorice, sunflower, horse chestnut, ginseng, oats, capsicum peppers, aubergine, tomato seed, alliums, asparagus, yam, fenugreek, *yucca* and ginseng, lucerne, mung beans, *Bupleurum falcatum, Camellia oleifera, Camellia sinensis Desmodium adscendens, Gypsophila, Panax quinqufolius, Panax japonicas, Quillaja saponaria, Sapindus delavayi, Sapindus mukorossi, Sapindus marginatus, Sapindus saponaria, Sapindus trifoliatus, Saponaria officinalis, Styrax japonica*, and *Yucca schidigera* or any mixture thereof. Any part of the plant may be used for extracting the saponin material, including leaves, stems, roots, bulbs, blossom and fruit (including the skin, flesh and seed of the fruit).

In some embodiments, the saponin material is an extract of *Camellia sinensis, Camellia oleifera, Saponaria officinalis*, or *Sapindus mukorossi* or a mixture thereof.

In other embodiments, the saponin material is an extract of *Camellia oleifera*, or *Sapindus mukorossi* or a mixture thereof.

In other embodiments, the saponin material is an extract of *Sapindus mukorossi*.

The saponin material obtained from a plant source, e.g., *Camellia oleifera*, and/or *Sapindus mukorossi*, may be extracted as disclosed hereinbelow. In some embodiments, the extraction process comprising: treating the plant source in a water/alcohol solution under conditions permitting extraction of the saponin material into the solution. The so-extracted saponin containing material may optionally thereafter be purified by any means known in the art, including: filtration, centrifugation, re-crystallization, distillation, adsorption, chromatographic methods, fractionation, etc.

In some embodiments, the plant source is first dried and ground before being treated in the water/alcohol solution.

In some embodiments, the saponin material is extracted from a plant source following a method comprising:
1. Treating the plant source in a 40:60 to 60:40 water:alcohol solution for a period of time and under conditions permitting extraction of the saponin material from said plant source into said solution, as defined hereinabove;
2. optionally, drying said saponin-containing solution to obtain a saponin-containing solid material; and
3. optionally, purifying said saponin-containing solid material.

In some embodiments, the water:alcohol solution employed is about 50:50.

In some embodiments, the plant source is one or both of *Camellia oleifera* and *Sapindus mukorossi*. In some embodiments, the plant source is *Sapindus mukorossi* and the saponin material is extracted from the nut shell. In other embodiments, the plant source is *Camellia oleifera* and in some embodiments the saponin material is extracted from the defatted seed meal of *Camellia oleifera*.

The at least one thickening agent is, according to some embodiments, a polysaccharide. In some embodiments, the polysaccharide is selected, in a non-limiting fashion, from xanthan gum (obtained by fermentation of *Xanthomonas campestris*), Tragacanth gum (which may be obtained from the dried sap of several species of Middle Eastern legumes of the genus *Astragalus*, including *A. adscendens, A. gummifer, A. brachycalyx* and *A. tragacanthus*), Carrageenan gum (Carrageenan being a cell wall hydrocolloid found in several species of seaweeds belonging to red algae of the class: Rhodophyceae), Alginates (which may be extracted from seaweed/Algea), Konjac gum (which may be obtained from konjac tree of the genus *Amorphophallus*), Agar-Agar (found in cell walls of agarophyte red algae), gum Arabic (which may be obtained of hardened sap taken from two species of the *acacia* tree: *Acacia senegal* and *Acacia seyal*, Guar gum (a primary component of the ground endosperm of guar beans) Starch (plant extracts), Gellan gum (produced by Sphingomonas elodea), Pectin (mainly from citrus and apple extract), Cellulose (from a variety of plants, tree pulp and cotton linters), Welan and Dituan gum (obtained by aerobic fermentation), Locust bean gum extract seeds of the carob tree, Dammar gum (obtained from the Dipterocarpaceae family of trees in India and East Asia, principally those of the genera Shorea, Balanocarpus or Hopea), Kauri gum (a fossilized resin detracted from kauri trees), Spruce gum (obtained from a the resin of spruce trees), gum from Fenugreek and gum anima (western or eastern).

In some embodiments, the at least one thickening agent is naturally-obtained gum Arabic, guar gum, Konjac gum, tragacanth gum, xanthan gum and carageenan.

In some embodiments, the composition of the invention comprises gum Arabic and/or guar gum. In other embodiments, the composition comprises Konjac gum and tragacanth gum. In further embodiments, the composition comprises xanthan gum and carageenan.

In some embodiments, the amount of the at least one polysaccharide, e.g., gum Arabic, is in the range of 0.1 and 8 wt % out of the total solid weight of the composition. In other embodiments, the amount is between 0.1 and 4 wt %.

In some embodiments, the amount of Konjac mannan is in the range of 0.1 to 5 wt % out of the total solid weight of the composition. In further embodiments, the amount is between 0.1 and 0.5 wt %.

In some embodiments, the amount of the guar gum is in the range of 0.1 to 5 wt % out of the total solid weight of the composition. In other embodiments, the amount is between 0.1 and 0.8 wt %.

In some embodiments, the amount of the tragacanth gum is in the range of 0 to 5 wt % out of the total solid weight of the composition. In some embodiments, the amount is between 0.1 and 0.4 wt %.

In some embodiments, the amount of the xanthan gum is in the range of 0 to 5 wt %. In other embodiments, the amount is between 0.1 and 0.5 wt %.

In some embodiments, the amount of the carraggenan is in the range of 0 to 5 wt %. In further embodiments, the amount is between 0.1 and 0.5 wt %.

The at least one naturally-obtained humectant is a hygroscopic substance selected amongst sugars and other polyols. Non-limiting examples of such humectants include fructose, mannose, sucrose, glucose, dextrose, trehalose, mannitol, lactose, rhamnose (which may be obtained from a great verity of plant sources), sorbitol (which may be extracted, e.g., from seaweed and various fruits such as grapes, cherries, plums, apples, apricots, peaches, dates) and honey extracts, glycol, diols and polyols such as vegetable glycerin, 1,2-butanediol, propylene glycol, ethanol (which may be obtained from plant extracts or via fermentation). In addition, betaine, natural urea, lactic acid and other alpha hydroxy acids (such as glycolic acid, citric acid, mandelic acid, tartaric acid), colloidal oat meal, Aloe vera, hyaluronic acid, Panthenol, pyroglutamic acid (PCA) and its salts, yeast and algea extract.

In some embodiments, in the composition of the invention, the at least one humectant is selected from a polyol, e.g., sorbitol. In other embodiments, the composition comprises ethanol and at least one polyol. The amount of the at least one polyol, e.g., sorbitol, may be in the range of 1 to 20 wt % out of the total solid weight of the composition. In some embodiments, the amount is 1 to 5 wt %.

Depending on the final application, the composition of the invention may comprise one or more active or inert natural additives. The at least one natural additive may be selected, in a non-limiting fashion, from acyclic sesquiterpene oligoglycosides (ASOGs), betain, a surfactant, a co-surfactant, a polysaccharide, a phospholipid, a bio-surfactant (such as Rhamnolipid), a moisturizer, an anti-irritation agent, an anti-oxidation agent, a mineral, a coloring agent, a perfume, a salt, a natural oil, and any combination thereof; wherein each of the aforesaid is naturally obtained.

In some embodiments of the invention, the composition comprises at least one acyclic sesquiterpene oligoglycosides (ASOGs), which may be obtained by extraction from the *Sapindus* species that are glycosides containing carbohydrate and sugar residues, as well as from other sources.

In some embodiments, the composition comprises betaine, trimethylaminoacetate glycine, which may be obtained for example from beets, broccoli and spinach. In some embodiments, the betaine is obtained from sugar beet. The amount of betaine in the composition may be in the range of 0 to 10 wt %. In some embodiments, the amount is between 2 and 8 wt %. In further embodiments, the amount is between 4 and 8 wt %.

In further embodiments, the composition of the invention may comprise at least one natural surfactant or bio-surfactant such as polypeptides (which may be obtained from animal sources such as egg, milk, whey, silk, algae, fish, collagen, gelatin, Elastin, Keratin and other sources; from herbal sources—proteins such as Leguminosae and Phocaea proteins obtained, for example, from pea, soy, chickpea, rice, wheat, peanut, quinoa, oat, lupine, and *Secale cereale*; or may be obtained by extracting beer, and hydrolyzed protein by fermentation), glycolipids, lipopeptides, phospholipids and fatty acids and polymeric compounds.

In some embodiments, the composition comprises at least one phospholipid. In some embodiments, the amount of the phospholipid is between 0 and 5 wt %. In further embodiments, the amount is between 0.5 and 3 wt %.

In some embodiments, the at least one surfactant is a biosurfactant, such as surfactin, rhamnolopids, and sophorolipids. In some embodiments, the amount of the biosurfactant, e.g., rhamnolipids, is in the range of 0 and 10 wt %. In further embodiments, the amount is between 0.5 and 4 wt %. In still other embodiments, the amount is between 0.5 and 2 wt %.

In some embodiments, the biosurfactant is rhamnolipids.

The at least one surfactant/bio-surfactant may be used in combination with a co-surfactants/secondary surfactant. Such co-surfactants may be selected amongst cholesterol, phytosterol, bile salts, glycyrrhizin, salt of glycyrrhizinate (may be derived from licorice root or hops extract (*Humulus lupulus*)).

The formulations of the invention may additionally contain at least one naturally-obtained moisturizer which may be selected amongst oily or non-oily agents. In some embodiments, the non-oily moisturizer is selected amongst natural urea, lactic acid (which may be produced by fermentation), and alpha hydroxy acids (which may be obtained from fruits or from fermentation). The moisturizer may alternatively be selected from betaine, natural urea, lactic acid and other alpha hydroxy acids (such as glycolic acid, citric acid, mandelic acid, tartaric acid), colloidal oat meal, Aloe vera, hyaluronic acid, panthenol, pyroglutamic acid (PCA) and salts thereof, yeast and algae extracts and other hygroscopic materials. In other embodiments, the composition of the invention comprises at least one oily moisturizer selected amongst herbal essential, vegetable oils and triglycerides. non-limiting examples of such include, almond oil, apricot oil, arachis oil, aragan oil, avocado oil, babchi oil, *calendula* oil, cucumber oil, castor oil, chirongi oil, coconut oil, evening prime rose oil, grape seed oil, hazel nut oil, hemp seed oil, hippophae rhamnoides oil, jojoba oil, kaluanji (black cumin) oil, karanj seed oil, linseed oil, macadamia oil, meadowfoam oil, moring a oil, musk melon oil, malknagni oil, madhuca indiaca oil, neem oil, olive oil, olive oil, pomegranate oil, poppy oil, pumpkin oil, palm oil, sesame seed oil, sun flower oil, vegetable squalane and squalane, walnut oil water melon oil, wheat germ oil, oil from eggs or yolk, jojoba wax, lanolin, bees wax, carnauba wax, candelilla wax, cocoa and animals wax/butter.

In some embodiments, the at least one natural moisturizer is Jojoba oil. In some embodiments, the amount of jojoba oil is in the range of 0 and 4 wt %. In some embodiments, the amount is between 0.1 and 4 wt %. In further embodiments, the amount is between 0.1 and 0.5 wt %.

The at least one natural additive may also be selected amongst anti-irritation plant extracts such as Chamomile extract, bisabolol, *Calendula* extract, Witch hazel extract, Khella extract, Euphrasia extract and amongst anti-oxidation plant extracts such as black current extract, olive leaf extract, vitamin C (ascorbic acid), vitamin E (tocopherols), *Wasabi* extract, *Lonicera* extract and pomegranate extract.

In some embodiments, the at least one additive is a natural mineral such as mud and clays. Generally speaking, the natural mineral may also be selected from Vegum (magnesium aluminum silicate), bentonite, Mica, Talk, Kaolin, and others.

In some embodiments, the composition comprises an inorganic salt and oxide of an atom selected from Na, K, Tin, Mg, Ca, Cr, Fe, Al, Co, Ni, Cu, Zn, Ag, Au, Pt, Zr, Ti, and Pb, with chloride, bromide, fluoride, iodide, sulfate and sulfite, sulphide, phosphate, silicate, hydroxide, carbonate, hydrcabonate, acetate, gluconate, and propionate, the salt being for example NaCl, KCl, $CaCl_2$, $MgSO_4$ and others.

In some embodiments, the amount of the salt, e.g., NaCl, is in the range of 0 to 10 wt %. In some embodiments, the amount is between 0.5 and 2 wt %.

In a further aspect of the present invention, there is provided an all-natural personal care formulation comprising a naturally-obtained saponin material, at least one naturally-obtained thickening agent, at least one naturally-obtained humectant, at least one naturally-obtained preservative and at least one naturally-obtained additive, each of which as defined herein.

In some embodiments, the personal care formulation is a cleansing liquid composition, which may be in the form of a liquid soap or shampoo, said formulation comprising saponin, one or more of betaine, at least one phospholipid, sorbitol, gum Arabic, guar gum, at least one salt (such as NaCl), at least one preservative, perfume, and optionally at least one oil.

In some embodiments, the personal care formulation further comprises one or more of Konjac gum, tragacanth gum, rhamnolipids and jojoba oil.

In further embodiments, the personal care formulation further comprises one or more of alga gel, xanthan gum and carrageenan.

In some embodiments, the saponin or any other surfactant may be in access in the final formulation.

The amount of the water in the natural liquid soap, cleaning composition or shampoo is added to 100%.

In some embodiments, in the personal care formulation the saponin material is an extract of *Sapindus Mukorossi* and/or an extract of *Camellia oleifera*. In some embodiments, said saponin material being obtained by extracting said plant material (*Sapindus Mukorossi* and/or an extract of *Camellia oleifera*) using a mixture of water/ethanol at a weight to weight ratio of between 40:60 to 60:40. In some embodiments, the water/ethanol mixture being at a weight to weight ratio of about 50:50.

In further embodiments, the liquid cleansing formulation comprises an extract of *Sapindus* Mukorossi, an extract of *Camellia oleifera* or a combination thereof, betaine, or phospholipid or a combination thereof, at least one polyol, at least one preservative, perfume and jojoba oil. The formulation may further comprise rhamnolipids (biosurfactant).

In some embodiments, the amount the extract of *Sapindus mukorossi* is in the range of 2 to 30 wt %. In other embodiments, the amount of each extract is between 5 and 30 wt %. In further embodiments, the amount is between 10 and 20 wt %.

In some embodiments, the amount of the extract of *Camellia oleifera* is in the range of 0 to 30 wt %. In other embodiments, the amount is between 0 to 10 wt %.

In some embodiments, the amount of the extract of *Sapindus Mukorossi* is in the range of 2 and 30 wt %, the amount of the extract of *Camellia oleifera* is in the range of 0 to 30 wt %, the amount of betaine is in the range 1 to 10 wt %, the amount of the at least one phospholipid is in the range of 0 to 5 wt %, the amount of the at least one humectant is in the range of 1 to 20 wt %, the amount of the rhamnolipids (biosurfactant) is in the range of 0 to 10 wt %, the amount of the at least one polysaccharide is in the range of 0.1 and 8 wt % and the amount of the at least one preservative is in the range 0.1 to 5 wt %, the amount of the perfume is in the range 0.1 to 5 wt %, and the amount of the at least one humectant is in the range of 0 to 10 wt %.

In some embodiments of the invention, the weight ratio of the saponin extract or saponin extracts (e.g., from *Sapindus mukorossi* and/or from *Camellia oleifera*) to the at least one phospholipid is 1:0.05 to 1:0.5.

In some embodiments, the weight ratio of the one or more saponin extract(s) to said at least one phospholipid and said betaine is 10.0:0.2:4.0.

In some embodiments, the formulations of the invention comprise at least one sugar such as glucose, fructose, sucrose, maltose, galactose and the like.

In some embodiments, the formulation of the invention further comprises at least one perfume. The perfume may contain one or more essential oils. The at least one essential oil may be selected in a non limiting fashion from the following essential oils: ambrette, angelica, anise, amyris, bay, bergamot, basil, bois-de-rose, cade, cajiput, camphor, cananga, java cassia, clary sage, curry, calamus, costus, carrot, cedar wood, cedar, cinnamon, citronella java, clove, cypress, cyperiol, chamomile blue, chamomile roman, davana, dill, elemi, eucalyptus, eucalyptus globules, frank incense, geranium, ginger grass, ginger lily, galangal, gurjam, grape fruit, jasminum, juniper berry, juniper, kapoor katcheri, lavender, lemon, lemon grass, lemon melissa, lime, laur spearmint, lemon balm, litsea cubeba, mentha citrata, mentha piperata, mentha shivalik, mandarin, marjoram, mint, myrtle, nar kachur, neroli, niaouli, orange, sweet orange, oregano, bitter patchouli, petit grain, peppermint, pine, palma rosa, pimento berry, rose wood, rose marry, rosemary, sandal wood, spearmint, sugandh mantri (gandhi roots), spike nard, tarragon, tangerine, tea tree, thyme, thuja wood, tomar (zanthozylum), tagettues, vetiver, valerian, winter green, worm wood (gaultheria fragrantissim wall), ylang ylang, zadoeria and any combination thereof.

In addition, or alternatively to the aforementioned essential oil, the formulation may comprise at least one additional plant extract selected from *wasabi*, black currant, aspen bark, *Lonicera* species, and others. In some embodiments, the amount of the perfume is in the range of 0.1 to 5 wt %.

The formulation may further comprise at least one natural preservative, which may be one or more of an extract of anise, black currant, cinnamon or cinnamon oil, geranium or geranium oil, ginger or ginger oil, Indian ginseng root, lavender, lemongrass, *Magnolia acnibio*, maritime pine, *Mentha piperita*, olive leaf, oregano, peppermint, elderberry, rosemary, tea tree, thyme and grapefruit. In some embodiments, the amount of the at least one preservative is in the range of 0.1 to 5 wt %.

The formulation may also comprise a natural extract, e.g., a plant extract from the one or more of the genus *Lonicera, Populus, Salix* and *Wasabia* or combination thereof. It should be understood that the extract may be an extract of more than one plant selected from *Lonicera, Populus, Salix* and *Wasabia* and that each plant may be selected from the same genus or from a different genus. It should be further that the present invention further contemplates composition comprising mixtures of extract, whether prepared and formulated individually or prepared in one-pot from a mixture of plant sources (plant parts).

The genus "*Lonicera*" contains a group of arching shrubs or twining vines in the family Caprifoliaceae that are commonly known as Honeysuckles. Known species include *Lonicera periclymenum* (European Honeysuckle or Woodbine), *Lonicera japonica* (Japanese Honeysuckle, White Honeysuckle, or Chinese Honeysuckle) and *Lonicera sempervirens* (Coral Honeysuckle, Trumpet Honeysuckle, or Woodbine Honeysuckle).

In some embodiments, the *Lonicera* extract is an extract of *Lonicera periclymenum* (European Honeysuckle or Woodbine), *Lonicera japonica* (Japanese Honeysuckle, White Honeysuckle, or Chinese Honeysuckle) and/or *Lonicera sempervirens* (Coral Honeysuckle, Trumpet Honeysuckle, or Woodbine Honeysuckle). In other embodiments, the *Lonicera* extract is an extract of *Lonicera japonica* (Japanese Honeysuckle, White Honeysuckle, or Chinese Honeysuckle).

The genus "*Populus*" comprises species of deciduous flowering plants in the family Salicaceae. Species of this genus include aspen (e.g., *Populus adenopoda, Populus alba, Populus grandidentata, Populus sieboldii, Populus tremula* and *Populus tremuloides*), and cottonwood (e.g., *Populus deltoids* L., *Populus fremontii* and *Populus nigra* L.).

In some embodiments, the *Populus* extract is an extract of aspen (e.g., *Populus* adenopoda, *Populus alba, Populus grandidentata, Populus sieboldii, Populus tremula* and *Populus tremuloides*), and/or cottonwood (e.g., *Populus deltoids* L., *Populus fremontii* and *Populus nigra* L.). In other embodiments, the *Populus* extract is an extract of aspen selected from *Populus adenopoda, Populus alba, Populus grandidentata, Populus sieboldii, Populus tremula* and *Populus tremuloides*. In other embodiments, the extract is of *Populus tremuloides*.

The genus "*Wasabia*" belonging to the Brassicaceae family includes inter alia the species *Wasabia japonica, Wasabia koreana, Wasabia tetsuigi, Wasabia tenuis, Wasabia bracteata, Wasabia okinosimensis, Wasabia pungens, Wasabia thibeticum* and *Wasabia yunnanensis*. In some embodiments, the *Wasabia* extract is an extract of *Wasabia japonica, Wasabia koreana, Wasabia tetsuigi, Wasabia tenuis, Wasabia bracteata, Wasabia okinosimensis, Wasabia pungens, Wasabia thibeticum* and/or *Wasabia yunnanensis*. In other embodiments, the *Wasabia* extract is an extract of *Wasabia japonica*.

The genus "*Salix*" belonging to the Salicaceae family specifically includes the species *Salix herbacea, Salix babylonica, Salix alba, Salix* x *sepulcralis* (weeping willow), and also includes inter alia the species *Salix aegyptiaca, Salix alaxensis, Salix alba, Salix amplexicaulis, Salix amygdaloides, Salix ansoniana, Salix apennina, Salix apoda, Salix appendiculata, Salix arbuscula, Salix arctica, Salix argyracea, Salix arizonica, Salix armenorossica, Salix atrocinerea, Salix aurita, Salix babylonica, Salix balfouriana, Salix barclayi, Salix bebbiana, Salix bicolor, Salix bikouensis, Salix bonplandiana, Salix boothii, Salix brachycarpa, Salix breviserrata, Salix breweri, Salix burqinensis, Salix caesia, Salix calcicola, Salix calliantha, Salix canariensis, Salix candida, Salix cantabrica, Salix capensis, Salix capitata, Salix caprea, Salix capusii, Salix carmanica, Salix caroliniana, Salix caspica, Salix cavaleriei, Salix chaenomeloides, Salix cinerea, Salix cordata, Salix delnortensis, Salix discolor, Salix drummondiana, Salix eastwoodiae, Salix eriocephala, Salix excelsa, Salix exigua, Salix fargesii, Salix floderusii, Salix fluviatilis, Salix foetida, Salix fragilis, Salix geyeriana, Salix gilgiana, Salix glabra, Salix glauca, Salix glaucosericea, Salix gooddingii, Salix gordejevii, Salix graciliglans, Salix gracilistyla, Salix hastata, Salix hegetschweileri, Salix helvetica, Salix herbacea, Salix hookeriana, Salix humboldtiana, Salix humilis, Salix hylematica, Salix integra, Salix irrorata, Salix japonica, Salix jejuna, Salix jepsonii, Salix jessoensis, Salix koreensis, Salix koriyanagi, Salix laevigata, Salix lanata, Salix lapponum, Salix lasiolepis, Salix lemmonii, Salix ligulifolia, Salix linearistipularis, Salix longiflora, Salix longistamina, Salix lucida, Salix lutea, Salix magnifica, Salix matsudana, Salix maximowiczii, Salix medwedewii, Salix melanopsis, Salix microstachya, Salix mielichhoferi, Salix miyabeana, Salix moupinensis, Salix mucronata, Salix muscina, Salix myricoides, Salix myrsinifolia, Salix myrsinites, Salix myrtilloides, Salix neowilsonii, Salix nigra, Salix nivalis, Salix orestera, Salix paraplesia, Salix pauciflora, Salix pedicellata, Salix pellita, Salix pentandra, Salix petiolaris, Salix phlebophylla, Salix phylicifolia, Salix planifolia, Salix polaris, Salix prolixa, Salix purpurea, Salix pyrenaica, Salix pyrifolia, Salix pyrolifolia, Salix rehderiana, Salix repens, Salix reptans, Salix reticulata, Salix retusa, Salix retusoides, Salix rorida, Salix rosmarinifolia, Salix sajanensis, Salix salviifolia, Salix schwerinii, Salix scouleriana, Salix sericea, Salix serissima, Salix serpyllifolia, Salix sessilifolia, Salix sitchensis, Salix siuzevii, Salix starkeana, Salix subopposita, Salix subserrata, Salix suchowensis, Salix sungkianica, Salix taxifolia, Salix tenuijulis, Salix tetrasperma, Salix triandra, Salix turanica, Salix turfacea, Salix udensis., Salix uva-ursi, Salix variegata, Salix vestita, Salix viminalis, Salix vulpina, Salix waldsteiniana, Salix wallichiana, Salix wilhelmsiana, Salix wilsonii, Salix yezoalpina*.

In some embodiments the extract of a species belonging to the *Salix* genus is an extract of *Salix alba*. In some embodiments the extract of a species belonging to the *Salix* genus is extracted from the leaves and in some embodiments it is extracted from the bark of the plant.

The extract from the above identified plant sources may be obtained from any part of the plant, including leaves, stems, roots, bulbs, blossom and fruit (including the skin, flesh and seed of the fruit).

In some embodiments, the formulation according to the invention comprises an extract from the nut of *Sapindus mukorossi*, the seed meal of *Camellia oleifera*, the flower and buds of *Lonicera japonica*, the root of *Wasabia japonica*, or the bark of *Populus tremuloides* or a combination thereof.

In some embodiments, the formulation according to the invention comprises an extract from the nut of *Sapindus mukorossi*, the seed meal of *Camellia oleifera*, the flower and buds of *Lonicera japonica*, the root of *Wasabia japonica*, the bark of *Salix* alba or a combination thereof.

In some embodiments, the formulation according to the invention comprises an extract from the nut of *Sapindus mukorossi*, the seed meal of *Camellia oleifera*, the flower and buds of *Lonicera japonica*, the root of *Wasabia japonica*, the bark of *Populus tremuloides*, the bark of *Salix alba* or a combination thereof.

In some embodiments, the formulation according to the invention comprises an extract from the nut of *Sapindus mukorossi*.

In some embodiments, the formulation according to the invention comprises an extract from the seed meal of *Camellia oleifera*.

In some embodiments, the formulation according to the invention comprises an extract from the flower and buds of *Lonicera japonica*.

In some embodiments, the formulation according to the invention comprises an extract from the root of *Wasabia japonica*.

In some embodiments, the formulation according to the invention comprises an extract from the bark of *Populus tremuloides*.

In other embodiments, each of the plant extracts is obtained commercially.

In some embodiments, the composition of the invention comprises a saponin material and at least one extract selected from *Lonicera japonica, Populus tremuloides* and *Wasabia japonica*.

In an embodiment of the invention, propionic acid is added to the preservative composition.

In some embodiments, the personal care formulation in accordance with the invention comprises an extract of *Sapindus mukorossi*, and/or an aqueous extract of *Camellia oleifera* or a combination thereof, betaine or at least one phospholipid or a combination thereof, sorbitol, gum Arabic, Konjac mannan, guar gum, NaCl, tragacanth gum, Rhamnolipids, jojoba oil, at least one preservative, a perfume and water.

In some embodiments, the formulation comprises an extract of *Sapindus mukorossi*, and/or an aqueous extract of *Camellia oleifera* or a combination thereof, betaine, sorbitol, gum Arabic, guar gum, NaCl, at least one preservative, a perfume and water.

In further embodiments, the formulation comprises an extract of *Sapindus mukorossi*, and/or an aqueous extract of *Camellia oleifera* or a combination thereof, at least one phospholipid, sorbitol, gum Arabic, guar gum, NaCl, at least one preservative, a perfume and water.

In further embodiments, the formulation comprises an extract of *Sapindus* mukorossi, and/or an aqueous extract of *Camellia oleifera* or a combination thereof, at least one phospholipid, betaine, sorbitol, gum Arabic, guar gum, NaCl, at least one preservative, a perfume and water.

In another aspect of the present invention, there is provided a liquid shampoo formulation comprising water and each of the following ingredients:

| | |
|---|---|
| *Sapindus mukurossi* fruit extract | (*Sapindus* extract) |
| *Camellia oleifera* seed extract | (*Camellia* extract) |
| Glycerin | (Vegetable glycerin) |
| Xanthan gum | (*Xanthomonas*) (fermentation) |
| Betaine | (Sugar beet extract) |
| Lecithin | (Soy or egg extract) |
| Aspen bark extract | (Aspen bark extract) |
| Natural Fragrance | (Plants extract) |
| Almond oil (optional) | (Almond plant) |
| Jojoba oil (optional) | (Jojoba plant) |
| Squalene (optional) | (Olive oil extract) |
| Lanolin (optional) | (Extract from wool) |

In a further aspect of the present invention, there is provided a liquid shampoo formulation comprising water and each of the following ingredients:

| | |
|---|---|
| *Sapindus mukurossi* fruit extract | (*Sapindus* extract) |
| *Camellia oleifera* seed extract | (*Camellia* extract) |
| Carrageenan | (Seaweeds extract) |
| Veegum | (Natural clay) |
| Colloidal oatmeal | (Oatmeal extract) |
| Lecithin | (Soy or egg extract) |
| Aspen bark extract | (Aspen bark extract) |
| Natural fragrance | (Plants extract) |
| Jojoba oil | (Jojoba extract) |
| Squalene | (Olive oil extract) |
| Betaine (optional) | (Sugar beet extract) |
| Glycerin (optional) | (Vegetable glycerin) |
| Sorbitol (optional) | (Fruit extract) |
| Honey (optional) | (Honey extract) |

In another aspect of the present invention, there is provided a liquid shampoo formulation comprising water and each of the following ingredients:

| | |
|---|---|
| *Sapindus mukurossi* fruit extract | (*Sapindus* extract) |
| *Camellia oleifera* seed extract | (*Camellia* extract) |
| Glycerin | (Vegetable glycerin) |
| Sorbitol | (Fruit extract) |
| Betaine | (Sugar beet extract) |
| Carrageenan | (Seaweeds extract) |
| Aspen bark extract | (Aspen bark extract) |
| Natural fragrance | (Plants extract) |
| Jojoba oil | (Jojoba extract) |
| Squalene | (Olive oil extract) |
| Lechitin | (Soy extract) |
| *Aloe Barbadensis* Leaf Juice | (*Aloe Barbadensis* Leaf Juice) |
| Urea | |
| Colloidal oatmeal | (Oat meal extract) |
| Veegum | (Natural clay) |
| Bentonite | (Natural clay) |

In another aspect of the present invention, there is provided a liquid shampoo formulation comprising water and each of the following ingredients:

| | |
|---|---|
| *Sapindus mukurossi* fruit extract | (*Sapindus* extract) |
| *Camellia oleifera* seed extract (optional) | (*Camellia* extract) |
| *Saponaria officinalis* root extract (optional) | (*Saponaria* extract) |
| Rhamnolipids (optional) | (*P. aeruginosa* extract) |
| Honey (optional) | (Honey extract) |
| Sorbitol (optional) | (Fruit extract) |
| Glycerol (optional) | (Vegetable glycerin) |
| Lactic acid (optional) | (Milk acid) |
| Betaine (optional) | (Sugar beet extract) |
| Taurocholate (optional) | (Bile salt) |
| *Aloe Barbadensis* Leaf Juice (optional) | (*Aloe Barbadensis* Leaf Juice) |
| Carrageenan | (Seaweeds extract) |
| Xanthan gum | (*Xanthomonas* fermentation) |
| Veegum | (Natural Clay) |
| Lecithin | (Soy or egg extract) |
| Colloidal oatmeal (optional) | (Oatmeal extract) |
| Natural fragrance | (Plants extract) |
| Aspen bark extract | (Aspen bark extract) |
| Jojoba oil (optional) | (Jojoba plant) |
| Squalene (optional) | (Olive oil extract) |

In another aspect of the present invention, there is provided a liquid shampoo formulation comprising water and each of the following ingredients:
  *Sapindus* extract
  *Camellia* extract
  Sorbitol Xanthan gum
Lecithin (optional)
Natural Fragrance
Aspen bark extract
Almond oil (optional)
Jojoba oil (optional)
Squalene (optional)
Chamomile $CO_2$ extract (optional)
Chamomile water extract (optional)

In another aspect of the present invention, there is provided a facial cleansing formulation comprising water and each of the following ingredients:
Sapindus extract
Ethanol (optional)
Sorbitol (optional)
Carrageenan
Xanthan Gum (optional)
Veegum (optional)
Betaine (optional)
Aspen bark extract
Natural Fragrance
Jojoba oil (optional)

In another aspect of the present invention, there is provided a facial cream formulation comprising water and each of the following ingredients:
Sapindus extract
Xanthan Gum
Carrageenan
Veegum
Aspen bark extract
Sorbitol
Shea Butter
Jojoba oil
Almond oil
Lecithin
Candelilla wax (optional)
Beeswax
Rice Starch In another aspect, the invention provides a method of extracting saponins from a saponin source (a plant source such as *Sapindus Mukorossi* and *Camellia oleifera*) using an alcohol/water solvent system.

In some embodiments, the extraction process comprising: treating the saponin source in a water/alcohol solution under conditions permitting extraction of the saponin containing material into the solution. The so-extracted saponin containing material may subsequently be purified by any means known in the art, including: filtration, centrifugation, re-crystallization, distillation, adsorption, chromatographic methods, fractionation, etc.

In some embodiments, the saponin material is extracted from a plant source following a method comprising:
1. Treating the plant source in a 40:60 to 60:40 water:alcohol solution for a period of time and under conditions permitting extraction of the saponin material from said plant source into said solution to obtain a solution of a saponin material;
2. Optionally evaporating said solution to obtain a solid saponin material; and
3. Optionally, purifying said solid saponin material.

As used herein, the "saponin-containing" solution or material comprises at least 0.2 wt % saponin compounds.

According to some embodiments, the extraction method is carried out by contacting the plant source, e.g., *Camellia oleifera* and *Sapindus mukorossi* with a 40:60 to 60:40 water/alcohol (e.g., ethanol) solution over a period of 2 to 8 hours. The extraction proceeds at room temperature (20° C. to 30° C.) and may be hastened by increasing the temperature above room temperature. In some embodiments, the extraction is carried out at a temperature above 30° C., 40° C., 50° C. or 60° C. In some embodiments, the extraction is carried out at a temperature between 30° C. and 70° C.

In some embodiments of the invention, the extraction solution is 50:50 water/ethanol. In further embodiments, the extraction is conducted for about 4 to 6 hours.

In some embodiments, the plant source is one or both of *Camellia oleifera* and *Sapindus mukorossi*. In some embodiments, the plant source is *Sapindus mukorossi* and the saponin material is extracted from the nut shell. In other embodiments, the plant source is *Camellia oleifera* and the saponin material is extracted from the defatted seed meal.

The saponin material (extract) obtainable by the above process of the invention has been found to be superior to saponin extracts obtained by other process of extraction as disclosed hereinbelow. For example, the saponin extract of the invention exhibits low surface tension and the best foaming ability, comparable only to a synthetic foaming agent, as exemplified hereinbelow. This characteristic, being essential in the formulation of personal care products, renders the use of the extract of the invention commercially important.

The novel saponin material of the invention may be used as a raw material in the manufacture of a variety of formulations, including: preservative formulations, disinfectant formulations, cosmetic formulations, therapeutic formulations, food additive formulations, and others.

In another aspect of the invention, there is provided a saponin-rich fraction obtainable from a plant source, e.g., *Sapindus mukorossi*, the fraction being characterized by having one or more of the saponin molecules which molecular weight and formula is listed in the table below:

| Retention Time (TIC), min | Measured mass | Atomic composition of $[M - H]^-$ |
|---|---|---|
| 22.49, 22.86 | 1015.4620 | $C_{45}H_{75}O_{25}$ |
| 22.60, 22.89, 23.27 | 1147.5026 | $C_{50}H_{83}O_{29}$ |
| 22.38, 22.90 | 1277.5641 | $C_{56}H_{93}O_{32}$ |
| 23.04, 26.05 | 1161.5203 | $C_{51}H_{85}O_{29}$ |
| 23.07, 25.91 | 1259.4937 | $C_{65}H_{79}O_{25}$ |
| 23.18, 24.30 | 853.4085 | $C_{39}H_{65}O_{20}$ |
| 23.24 | 985.4514 | $C_{44}H_{73}O_{24}$ |
| 23.70, 23.88 | 1243.4983 | $C_{65}H_{79}O_{24}$ |
| 24.24 | 1163.5364 | $C_{51}H_{87}O_{29}$ |
| 24.34, 25.7, 27.5, 27.8, 28.3, 28.9 | 1203.5301 | $C_{53}H_{87}O_{30}$ |
| 25.1, 26.4, 26.99 | 1187.5352 | $C_{53}H_{87}O_{29}$ |
| 24.9, 25.04 | 1159.5029 | $C_{51}H_{83}O_{29}$ |
| 25.42 | 1205.5422 | $C_{53}H_{89}O_{30}$ |
| 25.76, 27.11, 27.65, 27.9 | 1043.4918 | $C_{47}H_{79}O_{25}$ |
| 23.04, 26.0 | 1161.5186 | $C_{51}H_{85}O_{29}$ |
| 26.05, 27.36, 27.6, 28.1 | 1189.5522 | $C_{53}H_{89}O_{29}$ |
| 26.13, 26.61, 26.89 | 1041.4762 | $C_{47}H_{77}O_{25}$ |
| 24.51, 24.86, 26.25, 26.78, 27.16 | 1173.5198 | $C_{52}H_{85}O_{29}$ |
| 26.79 | 1201.5125 | $C_{53}H_{85}O_{30}$ |
| 24.97, 25.15, 26.35, 27.0 | 1285.5087 | $C_{67}H_{81}O_{25}$ |
| 27.17 | 707.3495 | $C_{33}H_{55}O_{16}$ |
| 27.70 | 1337.6369 | $C_{63}H_{101}O_{30}$ |
| 28.10 | 691.3550 | $C_{33}H_{55}O_{15}$ |
| 26.5, 27.0, 27.7, 28.3, 28.5, 29.0, 29.5, 29.7, 30.2 | 1229.5438 | $C_{55}H_{89}O_{30}$ |
| 28.7, 29.2, 29.9, 30.5, 31.1, 31.6, 31.8, 32.4 | 1271.5555 | $C_{57}H_{91}O_{31}$ |
| 27.93, 28.47, 29.12, 29.35, 30.19, 30.72 | 1085.5017 | $C_{49}H_{81}O_{26}$ |
| 29.6, 29.79, 30.74 | 1245.5395 | $C_{55}H_{89}O_{31}$ |
| 30.35, 30.65, 31.7, 31.9 | 1285.5344 | $C_{57}H_{89}O_{32}$ |

-continued

| Retention Time (TIC), min | Measured mass | Atomic composition of [M − H]⁻ |
|---|---|---|
| 31.11, 31.6, 32.23, 33.3 | 1313.5664 | $C_{59}H_{93}O_{32}$ |
| 30.0, 31.25 | 1273.5703 | $C_{57}H_{93}O_{31}$ |
| 31.39, 32.27, 32.61 | 1127.5128 | $C_{51}H_{83}O_{27}$ |
| 31.81, 33.09 | 1287.5518 | $C_{57}H_{91}O_{32}$ |
| 33.67, 34.76, 35.82, 37.02 | 1355.5768 | $C_{61}H_{95}O_{33}$ |
| 38.8-39.2 | 941.5156 | $C_{41}H_{81}O_{23}$ |
| 39.37 | 1071.5739 | $C_{54}H_{87}O_{21}$ |
| 39.53, 39.95 | 953.131 | $C_{49}H_{77}O_{18}$ |
| 40.2, 40.7, 41.1, 41.7, 43.1 | 863.4821 | $C_{46}H_{71}O_{15}$ |
| 42.73 | 603.3905 | $C_{35}H_{55}O_{8}$ |

DETAILED DESCRIPTION OF EMBODIMENTS

Examples

Example 1: Novel Saponin Material

Extraction of *Sapindus mukorossi* by Ethanol/Water Mixtures Determination of Foaming and Surface Tension Properties Experiment A 100 grams of dried pericarp of *Sapindus mukorossi* were dipped in 1000 ml distilled water in a mechanical stirrer, over night, at room temperature. The solution was filtered through Whatman 1, (Qualitative 110 mm×100 circles). The water mixture was expelled by Spray Dryer (SD-05, LabPlant, UK, pump rate: 0.01, inlet temperature 120° C., powdered temperature 70° C. and a white-brown powder was obtained. In order to measure the surface tension, the dry powder was dissolved in distilled water to form a concentration of 1 wt %. The same procedure was repeated with various ethanol/water mixtures.

Surface tension measurements were performed with an MGW-Lauda tensiometer (Lauda, Königshofen, Germany) equipped with a platinum plate. Each data point corresponds to the average of three measurements after a sufficient rest for equilibration. The same procedure was repeated with various ethanol/water mixtures.

The surface tension was measured and the results were as described in Table 1:

TABLE 1

Surface tension for the various ethanol/water extraction products

| water/ethanol mixture | surface tension (mN/m) |
|---|---|
| 100:0 | 43 |
| 80:20 | 48 |
| 60:40 | 44 |
| 50:50 | 36 |
| 40:60 | 35 |
| 20:80 | 39.5 |
| 0:100 | 40 |

Foaming properties of a solution of 1 wt % of the extract of the invention in water were measured by shaking 10 ml of the solution five times in a 100 ml covered glass cylinder. The volume of the generated foam was measured. Another method for measuring the foaming was performed by Moulinex LM240 blender at a maximum speed of 10 seconds for 80 ml solution. The generated foam was transferred to glass cylinder and measured. The same procedure was repeated with extracts obtained by various ethanol/water mixtures.

It was further found that a decrease in the surface tension led to an increase in the foaming ability and stability. The lowest surface tension was obtained when the plants were extracted by 60 wt % of ethanol and 40 wt % water or 50 wt % of ethanol and 50 wt % water.

TABLE 2

Foaming as a function of the water/ethanol mixture

| water/ethanol mixture | Foam by blender (ml) |
|---|---|
| 100/0 | 230 (±6) |
| 50/50 | 265 (±7) |
| 80/20 | 220 (±10) |

As may be noted from Table 2, the extract of the invention demonstrated even better foaming properties as compared to extracts obtained from the same plant source by similar methods.

Experiment B 100 grams of dried pericarp of *Sapindus Mukorossi* were dipped in 400 ml water/ethanol 100:0 (only water), 80:20, 30:70, 60:40, 50:50, 40:60, 70:30, 20:80 or 0:100 (ethanol 200 proof) (wt %/wt %) in a shaker (Innova 4000 incubator shaker, New Brunswick scientific, Edison, N.J. USA, rpm 183), for two hours. The shaker was heated to 60° C. The solution was filtered through Whatman 1, (Qualitative 110 mm Ø×100 circles). Then, the water mixture was expelled by Spray Dryer (SD-05, LabPlant, UK, pump rate: 0.01, inlet Temperature 120° C., powdered Temp 70° C.), and white-brown powdered was obtained.

Experiment C 100 grams of dried pericarp of *Sapindus Mukorossi* were dipped in 400 ml water/ethanol 50:50 (wt %/wt %) in a shaker (Innova 4000 incubator shaker, New Brunswick scientific, Edison, N.J. USA, rpm 183), for two, four or six hours. The shaker was heated to 60° C. The solution was filtered through Whatman 1, Qualitative 110 mm Ø×100 circles). Then, the water mixture was expelled by Spray Dryer (SD-05, LabPlant, UK, pump rate: 0.01, inlet temperature 120° C., powdered Temp 70° C.), and white-brown powdered was obtained. The yield was measured at between 17 and 31%.

Experiment D 100 grams of a seed cake of *Camellia oleifera* were dipped in 400 ml water/ethanol 50:50 (wt %/wt %) in a shaker (Innova 4000 incubator shaker, New Brunswick scientific, Edison, N.J. USA, rpm 183), for two, four or six hours. The shaker was heated to 60° C. The solution was filtered through Whatman 1, Qualitative 110 mm Ø×100 circles). Then, the water mixture was expelled by Spray Dryer (SD-05, LabPlant, UK, pump rate: 0.01, inlet temperature 120° C., powdered Temp 70° C.), and white-brown powdered was obtained. The yield was measured at between 17 and 22%.

The chemical composition of the saponin extract of the invention was evaluated as follows. HPLC analysis was performed on Accela High Speed LC system (Thermo Fisher Scientific Inc.) which consisted of Accela Pump, Accela Autosampler and Accela PDA detector.

Accela LC system was coupled with the LTQ Orbitrap Discovery hybrid FT mass spectrometer (Thermo Fisher Scientific Inc.) equipped with an electrospray ionization ion source. Mass spectrometer was operated in the negative ionization mode, ion source parameters were as follows: spray voltage 3.5 kV, capillary temperature 250° C., capillary voltage −35 V, source fragmentation was disabled, sheath gas rate (arb) 30, and auxiliary gas rate (arb) 10. Mass spectra were acquired in the m/z 200 to 2000 Da range.

The LC-MS system was controlled and data were analyzed using Xcalibur software (Thermo Fisher Scientific Inc.).

The chemical composition of a fraction of the saponin extract of the invention is listed in Table 3 below:

TABLE 3

The chemical composition of a saponin extract according to the present invention

| Retention Time (TIC), min | Measured mass | Atomic composition of [M − H]− |
| --- | --- | --- |
| 22.49, 22.86 | 1015.4620 | $C_{45}H_{75}O_{25}$ |
| 22.60, 22.89, 23.27 | 1147.5026 | $C_{50}H_{83}O_{29}$ |
| 22.38, 22.90 | 1277.5641 | $C_{56}H_{93}O_{32}$ |
| 23.04, 26.05 | 1161.5203 | $C_{51}H_{85}O_{29}$ |
| 23.07, 25.91 | 1259.4937 | $C_{65}H_{79}O_{25}$ |
| 23.18, 24.30 | 853.4085 | $C_{39}H_{65}O_{20}$ |
| 23.24 | 985.4514 | $C_{44}H_{73}O_{24}$ |
| 23.70, 23.88 | 1243.4983 | $C_{65}H_{79}O_{24}$ |
| 24.24 | 1163.5364 | $C_{51}H_{87}O_{29}$ |
| 24.34, 25.7, 27.5, 27.8, 28.3, 28.9 | 1203.5301 | $C_{53}H_{87}O_{30}$ |
| 25.1, 26.4, 26.99 | 1187.5352 | $C_{53}H_{87}O_{29}$ |
| 24.9, 25.04 | 1159.5029 | $C_{51}H_{83}O_{29}$ |
| 25.42 | 1205.5422 | $C_{53}H_{89}O_{30}$ |
| 25.76, 27.11, 27.65, 27.9 | 1043.4918 | $C_{47}H_{79}O_{25}$ |
| 23.04, 26.0 | 1161.5186 | $C_{51}H_{85}O_{29}$ |
| 26.05, 27.36, 27.6, 28.1 | 1189.5522 | $C_{53}H_{89}O_{29}$ |
| 26.13, 26.61, 26.89 | 1041.4762 | $C_{47}H_{77}O_{25}$ |
| 24.51, 24.86, 26.25, 26.78, 27.16 | 1173.5198 | $C_{52}H_{85}O_{29}$ |
| 26.79 | 1201.5125 | $C_{53}H_{85}O_{30}$ |
| 24.97, 25.15, 26.35, 27.0 | 1285.5087 | $C_{67}H_{81}O_{25}$ |
| 27.17 | 707.3495 | $C_{33}H_{55}O_{16}$ |
| 27.70 | 1337.6369 | $C_{63}H_{101}O_{30}$ |
| 28.10 | 691.3550 | $C_{33}H_{55}O_{15}$ |
| 26.5, 27.0, 27.7, 28.3, 28.5, 29.0, 29.5, 29.7, 30.2 | 1229.5438 | $C_{55}H_{89}O_{30}$ |
| 28.7, 29.2, 29.9, 30.5, 31.1, 31.6, 31.8, 32.4 | 1271.5555 | $C_{57}H_{91}O_{31}$ |
| 27.93, 28.47, 29.12, 29.35, 30.19, 30.72 | 1085.5017 | $C_{49}H_{81}O_{26}$ |
| 29.6, 29.79, 30.74 | 1245.5395 | $C_{55}H_{89}O_{31}$ |
| 30.35, 30.65, 31.7, 31.9 | 1285.5344 | $C_{57}H_{89}O_{32}$ |
| 31.11, 31.6, 32.23, 33.3 | 1313.5664 | $C_{59}H_{93}O_{32}$ |
| 30.0, 31.25 | 1273.5703 | $C_{57}H_{93}O_{31}$ |
| 31.39, 32.27, 32.61 | 1127.5128 | $C_{51}H_{83}O_{27}$ |
| 31.81, 33.09 | 1287.5518 | $C_{57}H_{91}O_{32}$ |
| 33.67, 34.76, 35.82, 37.02 | 1355.5768 | $C_{61}H_{95}O_{33}$ |
| 38.8–39.2 | 941.5156 | $C_{41}H_{81}O_{23}$ |
| 39.37 | 1071.5739 | $C_{54}H_{87}O_{21}$ |
| 39.53, 39.95 | 953.131 | $C_{49}H_{77}O_{18}$ |
| 40.2, 40.7, 41.1, 41.7, 43.1 | 863.4821 | $C_{46}H_{71}O_{15}$ |
| 42.73 | 603.3905 | $C_{35}H_{55}O_{8}$ |

*Sapindus* Extract Composition

The extracted powder of *Sapindus mukorossi* was further analyzed to identify its components.

The saponins and glycosides were analyzed by HPLC and LC-MS. The HPLC (Surveyor, Thermo, Calif., USA) was configured using Luna 5µ C18 (2) 100A (Phenomenex 00G-4252-E0). Saponins and glycosides were eluted from 16% acetonitrile and 84% water to 84% acetonitrile and 16% water with a 60-minute gradient. The flow rate was of 1 mL/minutes. Accela LC system was coupled with the LTQ Orbitrap Discovery hybrid FT mass spectrometer (Thermo Fisher Scientific Inc.) equipped with an electrospray ionization ion source. Mass spectrometer was operated in the negative ionization mode, ion source parameters were as follows: spray voltage 3.5 kV, capillary temperature 250° C., capillary voltage −35 V, source fragmentation was disabled, sheath gas rate (arb) 30, and auxiliary gas rate (arb) 10. Mass spectra were acquired in the m/z 200 to 2000 Da range. The LC-MS system was controlled and data were analyzed using Xcalibur software (Thermo Fisher Scientific Inc.).

Saponins and glycosides content and identification: HPLC and LC-MS studies showed that the main glycosides present in the *Sapindus mukorossi* extract were saponins derived from the triterpenes hederagenin and oleanolic acid, as well as acyclic sesquiterpene oligoglycosides (ASOG's). In the extract obtained from 50:50 wt % water/ethanol, the saponins content was 20 wt % (+10%), and the ASOG's content was 25 wt % (+10%). This saponin-rich extract is an extract according to the invention.

Example 2: Evaluations of *Sapindus mukorossi* Extract Concentrations in Water (I) *Sapindus mukorossi* Extract 5 Wt %

A cleansing composition: 5 grams of an extract powder from *Sapindus* Mukorossi dispersed in 100 ml distilled water and mixed at room temperature until a clear solution was formed. The extractions conditions was: extraction by ethanol/water 50:50 v %/v % at 60° C., the nuts/extraction solvent ratio 1:4, for 6 hours) and 0.5 ml $NaHCO_3$ 1M were added to the final extract.

Foaming—solution of 1 wt % of the extract in water was shaken five times in a glass cylinder as described above. The volume of the generated foam was measured. Another method for measuring the foaming was performed by Moulinex LM240 blender at a maximum speed of 10 seconds for 80 ml solution and measured in a glass cylinder, and the foaming results are detailed in Table 4 below.

(II) *Sapindus mukorossi* Extract 10 Wt %

10 grams of extract powder from *Sapindus mukorossi* (extraction by ethanol/water 50:50 wt %/wt % at 60° C., nuts/extraction solvent 1:4, for 6 hours,) and 1 ml of $NaHCO_3$ 1M were dispersed in 100 ml distilled water and mixed at room temperature until a clear solution was formed. The foaming was evaluated as mentioned above, and the foaming results are detailed in Table 4 below.

(III) *Sapindus mukorossi* Extract 15 Wt %

15 grams of extract powder from *Sapindus Mukorossi* (extraction by 50 wt % ethanol and 50 wt % water, 60° C. the nuts/extraction solvent 1:4, for 6 hours) and 1.5 ml of $NaHCO_3$ 1M were dispersed in 100 ml distilled water and mixed at room temperature until clear solution was formed. The foaming was evaluated as mentioned above, and the foaming results are detailed in Table 4 below.

(IV) *Sapindus mukorossi* Extract 20 Wt %

20 grams of extract powder from *Sapindus mukorossi* (extraction by 50 wt % ethanol and 50 wt % water, 60° C., nuts/extraction solvent 1:4, for 6 hours) and 1.5 ml of $NaHCO_3$ 1M were dispersed in 100 ml distilled water and mixed at room temperature until clear solution was formed. The foaming was evaluated as mentioned above, and the foaming results are detailed in Table 4 below.

TABLE 4

Foaming as a function of *Sapindus mukorossi* extract concentration

| Formulation | Foam volume by shaking (ml) | Foam volume by blender (ml) |
|---|---|---|
| 5 wt % *Sapindus mukorossi* extract | 40 (±1) | 227 (±7) |
| 10 wt % *Sapindus mukorossi* extract | 40 (±4) | 270 (±7) |
| 15 wt % *Sapindus mukorossi* extract | 46 (±4) | 350 (±10) |
| 20 wt % *Sapindus mukorossi* extract | 50 (±4) | 390 (±10) |

As the results indicate, all four formulations tested exhibited foaming necessary for certain formulations in accordance with the invention.

Example 3: Evaluations of Saponin Extract from Different Plants

In order to compare the foaming ability of the extract of the invention to commercially available saponins and to saponins obtained by methods different from that of Example 1 above, 1 wt % of calculated saponins from the plants: *Sapindus mukorossi*, Soy (Jieliang Extract LTD, China), *Yucca* (Sinerga, Italia), Fenugreek (Natural Remedies, India), tribulus (Natural Remedies, India), and *Quillaja* (Desert King, Chile), and synthetic surfactant; decyl glycoside (Cognis, Germany) were dispersed in 100 grams distilled water and mixed at room temperature until clear solution was formed (Soy, Fenugreek and tribulus are not well soluble). The foaming was evaluated as mentioned above, and the foaming results are detailed in Table 5 below.

TABLE 5

Foaming as a function of the saponin extracts from different plants

| Extract | Foam volume by shaking (ml) | Foam volume by blender (ml) |
|---|---|---|
| 1 wt % saponins from *Yucca* extract | 19 (±2) | 197 (±5) |
| 1 wt % saponins from Fenugreek extract | 16 (±2) | 170 (±5) |
| 1 wt % saponins from Soy extract | 18 (±1) | 185 (±5) |
| 1 wt % saponins from *tribulus* extract | 20 (±2) | 170 (±5) |
| 1 wt % saponins from *Quillaja* extract | 21 (±2) | 232 (±10) |
| 1 wt % saponins from *Sapindus Mukorossi* extract - prepared according to Example 1 | 63 (±2) | 390 (±17) |
| 1 wt % Decyl glycoside | 57 (±5) | 420 (±15) |

As can been seen from Table 5, the best foaming capability was obtained when using the *Sapindus Mukorossi* extract prepared according to Example 1, even in compared to the synthetic surfactant decyl glucoside.

The formulation of the present example has also been prepared with Aspen bark extract.

Example 4: Formulation Containing Betaine, Gum Arabic and Sorbitol with *Sapindus Mukorossi* Extract. Effect on the Foaming, Body, Hand Smooth, Dryness and after Feel Betaine—

8 grams of betaine in a powder form and 20 grams of *Sapindus Mukorossi* extract (extracted by 50 wt % ethanol and 50 wt % water, 60° C., nuts/extraction solvent 1:4, for 6 hours) together with 2 ml of $NaHCO_3$ 1M were separately dispersed in 100 ml distilled water and mixed at room temperature until two clear solutions were formed. Then, the two solutions were mixed together at amounts of 10 wt % *Sapindus* extract and 4 wt % betaine and stirred for two hours, at room temperature.

The following formulations were tested on 5 adults volunteers (men and woman). The volunteers washed they hand with the formulation using a foam pump (WaterGuard line, Rexam, UK). After washing the volunteers graded the following criteria.

The following properties of the personal care formulations have been tested:

The smoothness, "body" (reflects the consistency of the composition), dryness and "after feel" (reflects sensory feeling of fresh and clean appearance, silky, and soft afterfeeling) were assessed by 5 volunteers after washing hands (or hair).

The evaluation criteria were as follows:

5: excellent smoothness, foam body, foam stability and excellent after feel

4: good smoothness, body, foam stability and good after feel

3: some smoothness, body, foam stability and some after feel

2: poor smoothness, body, foam stability and poor after feel

1: no smoothness, body, foam stability and no after feel

The results are shown in Table 6.

Gum Arabic (1 wt %)—

Two grams of gum Arabic in a powder form and 20 grams of *Sapindus mukorossi* extract (extracted by 50% ethanol in water, powder/extraction solvent 1:4, 60° C., for 6 hours) together with 2 ml of $NaHCO_3$ 1M were separately dispersed in 100 ml distilled water and mixed at room temperature until two clear solutions were formed. Then, the two solutions were mixed together at amounts of 10 wt % *Sapindus mukorossi* extract and 1 wt % gum Arabic and stirred for two hours, at room temperature.

The foaming and the shampoo properties were evaluated as previously described. Results are the results are shown in Table 6.

Gum Arabic (3 wt %)—

6 grams of gum Arabic in a powder form and 20 grams of *Sapindus mukorossi* extract (extracted by 50 wt % ethanol in water, 60° C., the powder/extraction solvent ratio 1:4, for 6 hours) together with 2 ml of $NaHCO_3$ 1M were separately dispersed in 100 ml distilled water and mixed at room temperature until two clear solutions were formed. Then, the two solutions were mixed together at amounts of 10 wt % *Sapindus Mukorossi* extract and 3 wt % gum Arabic and stirred for two hours, at room temperature.

The foaming and the shampoo properties were evaluated as previously described. Results are shown in Table 6.

Sorbitol—

10 grams of sorbitol form and 20 grams *Sapindus Mukorossi* extract (extraction by 50% ethanol, nuts/extraction solvent 4:1, 60° C., for 6 hours) were separately dispersed in 100 ml distilled water and mixed at room temperature until two clear solutions were formed. Then, the two solutions were mixed together at amounts of 10 wt % *Sapindus mukorossi* extract and 5 wt % sorbitol and stirred for two hours, at room temperature.

The foaming and the formulation properties were evaluated as described before. Results are shown in Table 6.

TABLE 6

The foaming as a function of different ingredients at different concentrations

|  | Foam height by shaking (ml) | Foam height by blender (ml) | Body | Smoothness on hands | dryness | After feel |
|---|---|---|---|---|---|---|
| Sapindus 10% | 40 (±4) | 270 (±7) | 2 | 2 | 2 | 2 |
| Sapindus + betaine 10/4 | 42 (±4) | 290 (±2) | 3 | 3 | 3 | 2.5 |
| Sapindus + GA 10/1 | 35 (±4) | 268 (±2) | 3 | 3.5 | 3 | 3 |
| Sapindus + GA 10/3 | 38 (±6) | 270 (±2) |  |  |  |  |
| Sapindus + sorbitol 10/5 | 45 (±4) | 270 (±5) | 3 | 3 | 3 | 3 |

As shown in Table 6, the addition of betaine, gum Arabic (GA) and sorbitol did not cause significant deterioration in foam heights. However, it was found that, the "body" of the foam, the smooth-on-hand feeling, and the after feel were much better when betaine, GA or sorbitol were added, as compared to samples with only 10 wt % *Sapindus mukorossi* extract.

The formulation of the present example has also been prepared with Aspen bark extract.

Example 5: Formulations Containing Varying Amounts of *Sapindus* Extracts: Effect On Shampoo Performance The effect of the *Sapindus mukorossi* extract concentration on the shampoo performance was tested as described in Example 4. The shampoo was prepared as set forth in Table 7.

TABLE 7

Shampoo composition with varying amounts of *Sapindus Mukorossi* Extract

| Concentration | Exp. 1 (% wt) | Exp. 2 (% wt) | Exp. 3 (% wt) |
|---|---|---|---|
| Extract of *Sapindus Mukorossi* (ex. 2, 6 h) | 10 | 15 | 20 |
| Betaine | 4 | 4 | 4 |
| Sorbitol | 5 | 5 | 5 |
| Gum Arabic | 1 | 1 | 1 |
| Konjac gum | 0.375 | 0.375 | 0.375 |
| Guar gum | 0.375 | 0.375 | 0.375 |
| Whey protein | 1 | 1 | 1 |
| Water | 58.25 | 63.25 | 68.25 |

The shampoo formulation of Table 7 was tested as described in Example 4. The results of foaming and after feel obtained for the shampoo compositions 1 to 3 of Table 7 are summarized in Table 8 below.

TABLE 8

Properties defined for Shampoo formulation of Table 6

|  | "Body" | Smooth On hand | Foam stability | Ease of rinsing easily | After feel |
|---|---|---|---|---|---|
| 10% *Sapindus* extract | 2 | 2 | 2 | 4 | 2 |
| 1 | 3 | 4-5 | 4-5 | 4 | 3 |

TABLE 8-continued

Properties defined for Shampoo formulation of Table 6

|  | "Body" | Smooth On hand | Foam stability | Ease of rinsing easily | After feel |
|---|---|---|---|---|---|
| 2 | 3 | 4-5 | 4 | 4 | 3 |
| 3 | 3-4 | 4-5 | 4 | 4 | 3 |

The results demonstrate that there was some improvement in the feel of the composition when the concentration of the *Sapindus mukorossi* extract was increased from 10 to 20% wt, but the foam "body" improved more significantly upon an increase in the *Sapindus mukorossi* concentration.

The formulation of the present example has also been prepared with Aspen bark extract.

Example 6: Shampoo Formulations Comprising Various *Sapindus mukorossi* Extracts The effect of the *Sapindus mukorossi* extraction process as described in Example 1 on the shampoo performance was tested as a shampoo on babies' heads and evaluated as described at Example 4. The shampoo was prepared as set forth in Table 8, with different *Sapindus mukorossi* extracts according to Table 9.

TABLE 9

Various extractions employed in the preparation of shampoo formulations tested

|  | Exp. | | | | | | |
|---|---|---|---|---|---|---|---|
|  | 1 | 2 | 3 | 3 | 5 | 6 | 7 |
| Water/ethanol wt ratio | 70:30 | 50:50 | 30:70 | 50:50 | 50:50 | 50:50 | 50:50 |
| Extraction time (hr) | 2 | 2 | 2 | 4 | 6 | 2 | 2 |
| Extraction Temp. (° C.) | 60 | 60 | 60 | 60 | 60 | 40 | 60 |
| Extraction pH | 6.5 | 6.5 | 6.5 | 6.5 | 6.5 | 6.5 | 7 |

The average overall score by 5 volunteers using the shampoo compositions are listed in Table 10.

TABLE 10

Properties defined for Shampoo formulations of Table 9

| Ex. # | "Body" | Smooth On hair | Foam stability | Ease of rinsing easily | After feel |
|---|---|---|---|---|---|
| 1 | 4 | 4 | 4 | 5 | 4 |
| 2 | 4 | 4.5 | 5 | 5 | 4 |
| 3 | 4 | 4.5 | 4.5 | 5 | 4 |
| 4 | 4 | 4.5 | 4.5 | 5 | 4 |
| 5 | 4 | 4 | 4 | 5 | 4 |
| 6 | 4 | 4.5 | 4.5 | 4 | 4 |
| 7 | 4 | 4 | 4.5 | 5 | 4 |

Therefore, the best performance of the shampoo is obtained from the saponins extracts as described in the above table, Example 2, extraction by water/ethanol 50/50.

The formulation of the present example has also been prepared with Aspen bark extract.

Example 7: Shampoo Formulations Containing Various Saponin Types

The effect of the saponin material extracted from different plants was tested was tested as described in Example 4. The shampoo included the components set forth in Table 11.

TABLE 11

Shampoo base formulation for use with various saponins

| | Concentration (wt %) |
|---|---|
| Saponins extract | 5 |
| Betaine | 4 |
| Sorbitol | 5 |
| Gum Arabic | 2 |
| xanthan gum | 0.3 |
| NaCl | 1 |
| Water | 82.7 |

The shampoo composition detailed in Table 11 was prepared using different saponin extracts, as detailed in Table 12. The body, foaming, smoothness and after feel properties as a function of the type of saponin extract were evaluated by 5 volunteers, as described in Example 4. The results are tabulated in Table 12.

TABLE 12

Shampoo properties as a function of the saponins source

| Plant source of the saponins extract | Body | Smoothness | Foam stability | After feel |
|---|---|---|---|---|
| Yucca | 2 | 3 | 3 | 3 |
| Fenugreek | 1 | 3 | 2 | 3 |
| Tribulus | 1 | 3 | 2 | 3 |
| Quillaja | 4 | 3 | 4 | 2 |
| Soy | 1 | 4 | 2 | 3 |
| Sapindus mukorossi | 4 | 4 | 4 | 3-4 |

While the use of all saponin materials afforded excellent shampoo compositions, as can be seen from Table 12, the best quality shampoo was obtained by using the saponin extract according to the present invention (from *Sapindus mukorossi*).

The formulation of the present example has also been prepared with Aspen bark extract.

Example 8: Formulations Containing Polysaccharides and Humectants

The effect of polysaccharides and humectants on the formulations of the invention was tested in the following shampoo formulations. In each test, one of the ingredients was replaced by water, as described in Table 13. The preparation of the shampoo was performed according to Example 5. The shampoo properties were evaluated as described before in Example 4.

TABLE 13

Formulations with polysaccharides and polyols

| Concentration | 1 (% wt) | 2 (% wt) | 3 (% wt) | 4 (% wt) | 5 (% wt) | 6 (% wt) |
|---|---|---|---|---|---|---|
| Extract of Sapindus Mukorossi (example 2, 6 h) | 10 | 10 | 10 | 10 | 10 | 10 |
| Betaine | 0 | 4 | 4 | 4 | 4 | 4 |
| Sorbitol | 5 | 5 | 0 | 5 | 5 | 5 |
| Gum Arabic | 1 | 0 | 1 | 1 | 1 | 1 |
| Konjac gum | 0.375 | 0.375 | 0.375 | 0 | 0.375 | 0.375 |
| Guar gum | 0.375 | 0.375 | 0.375 | 0.375 | 0.375 | 0 |
| Whey protein | 1 | 1 | 1 | 1 | 0 | 1 |
| Water | 82.25 | 79.25 | 83.25 | 78.6 | 79.25 | 78.6 |

The results of foaming and after feel are shown in Table 14.

TABLE 14

Properties defined for the shampoo formulations of Table 12

| Experiment | Body | Smooth On hand | Foam stability | Rinsed easily | After feel |
|---|---|---|---|---|---|
| 1 | 3 | 4 | 3 | 4 | 3 |
| 2 | 2-3 | 4 | 3-4 | 4 | 2-3 |
| 3 | 3 | 3-4 | 3-4 | 4 | 3 |
| 4 | 2-3 | 3-4 | 4 | 4 | 3-4 |
| 5 | 3 | 3 | 4 | 4 | 3 |
| 6 | 3-4 | 2 | 4 | 4 | 2 |

The results presented in Table 14 demonstrate that when guar gum or gum Arabic were not included in the composition, the smoothness and the after feel of the composition were inferior. When konjac gum was not included, the decrease in the smoothness was less significant, and when betaine, or sorbitol, or gum Arabic were not included in the composition, the foam stability was decreased.

The formulation of the present example has also been prepared with Aspen bark extract.

Example 9: Formulations Containing Gum Arabic at Varying Concentrations

The effect of gum Arabic concentration on performance was tested in the shampoo formulations of Example 5.

The shampoo was prepared with or without gum Arabic as shown in Table 15.

TABLE 15

Composition with/without gum Arabic

| Concentration | Without gum Arabic (% wt) | With Arabic gum (% wt) |
|---|---|---|
| Extract of Sapindus Mukorossi (Example 2, 6 h) | 10 | 10 |
| Betaine | 4 | 4 |
| Sorbitol | 5 | 5 |
| Gum Arabic | 0 | 4 |
| Konjac gum | 0.375 | 0.375 |
| Guar gum | 0.375 | 0.375 |
| Whey protein | 1 | 1 |
| Water | 58.25 | 63.25 |

The results of the experiment, as set forth in Table 15, demonstrate that an increase in the gum Arabic concentration from 0 to 4% resulted in an improvement in the "body" and in the foam stability. However, for some other formulations of the invention, gum Arabic was not necessary.

TABLE 16 properties defined for the formulations of Table 15

| Exp. | Body | Smooth On hand | Foam stability | After feel |
|---|---|---|---|---|
| Without Arabic gum | 2-3 | 4 | 3-4 | 2-3 |
| With Arabic gum | 4 | 4 | 4 | 3 |

The formulation of the present example has also been prepared with Aspen bark extract.

Example 10: Formulations Containing Various Betaine Concentrations

The effect of betaine concentration on performance was tested in the following shampoo formulations. The results are shown in Table 17.

TABLE 17

Shampoo compositions with varied concentrations of betaine

|  | Betaine Concentration | | |
| --- | --- | --- | --- |
|  | 2% wt | 4% wt | 8% wt |
| Extract of *Sapindus mukorossi* % wt | 10 | 10 | 10 |
| Betaine % wt | 2 | 4 | 8 |
| Sorbitol % wt | 5 | 5 | 5 |
| Gum Arabic % wt | 1 | 1 | 1 |
| Konjac gum % wt | 0.375 | 0.375 | 0.375 |
| Guar gum % wt | 0.375 | 0.375 | 0.375 |
| Whey protein % wt | 1 | 1 | 1 |
| Water % wt | 58.25 | 58.25 | 63.25 |

The performance of the shampoo compositions of Table 17 were evaluated as described in Example 4 and the results are presented in Table 18.

TABLE 18

Shampoo properties

| Experiments | Body | Smooth on hand | Foam stability | After feel |
| --- | --- | --- | --- | --- |
| No betaine | 3 | 4 | 3 | 3 |
| Betaine (2% wt) | 4 | 3-4 | 3 | 3 |
| Betaine (4% wt) | 3-4 | 4 | 4 | 4 |
| Betaine (8% wt) | 4-5 | 4 | 4 | 3 |

The results indicate that an increase in the betaine concentration resulted in a slight improvement in the "body" and in the foam stability and after feel.

The formulation of the present example has also been prepared with Aspen bark extract.

Example 11: Formulations Comprising Konjac Gum TG

In order to assess the effect of the Konjac gum and TG was tested as described in Example 4. In Experiment 1, the shampoo was prepared with 0.375 wt % kanjac mannan gel, in Experiment 2 the shampoo was prepared with 0.375 wt % kanjac mannan powder food and in Experiment 3, the shampoo was prepared with 0.375 wt % tragacanth gum (TG) instead of konjac gum (Table 19).

TABLE 19

Shampoo formulation comprising TG and Konjac gum

| Concentration | Exp. 1 (% wt) | Exp. 2 (% wt) | Exp. 3 (% wt) |
| --- | --- | --- | --- |
| Extract of *Sapindus mukorossi* | 20 | 20 | 20 |
| Betaine | 4 | 4 | 4 |
| Sorbitol | 5 | 5 | 5 |
| Gum Arabic | 1 | 1 | 1 |
| Guar gum | 0.375 | 0.375 | 0.375 |
| Konjac mannan gel | 0.375 | 0 | 0 |
| Konjac mannan | 0 | 0.375 | 0 |
| TG | 0 | 0 | 0.375 |
| Water | 69.625 | 69.625 | 69.625 |

The results as set forth in Table 20 show that addition of konjac mannan food and TG increased the shampoo quality, especially by increasing the smoothness in the hand.

TABLE 20

Shampoo properties

| Experiments | Body | Smooth On hand | Foam stability | After feel |
| --- | --- | --- | --- | --- |
| 1 | 4 | 4 | 4 | 4 |
| 2 | 4 | 5 | 4 | 4 |
| 3 | 4 | 4-5 | 4 | 4 |

The formulation of the present example has also been prepared with Aspen bark extract.

Example 12: Formulations Comprising NaCl

The effect of a salt such as NaCl on the shampoo performance was tested in the following shampoo formulations (Table 21).

TABLE 21

Shampoo composition

| Concentration | (% wt) |
| --- | --- |
| Extract of *Sapindus Mukorossi* (ex. 2, 6 h) | 20 |
| Betaine | 2 |
| Sorbitol | 2.5 |
| Gum Arabic | 2 |
| Guar gum | 0.5 |
| TG | 0.2 |
| Konjac mannan powder food | 0.2 |
| NaCl | 1 |
| Water | 71.6 |

The results as set forth in Table 22 show that the addition of NaCl provided the shampoo with good body, smoothness, foam stability and after feel.

TABLE 22

Shampoo properties

| | Body | Smoothness | Foam stability | After feel |
| --- | --- | --- | --- | --- |
| Without NaCl | 4 | 4-5 | 4 | 4 |
| With NaCl | 4-5 | 4-5 | 4 | 4 |

The formulation of the present example has also been prepared with Aspen bark extract.

Example 13: Formulations Comprising Phospholipids

The effect of phospholipids (PHOSPHOLIPON 50, Lipoid, Germany) on the performance was tested in the following shampoo formulation (Table 23).

TABLE 23

| Shampoo composition | |
|---|---|
| Concentration | (% wt) |
| Extract of Sapindus Mukorossi | 20 |
| Betaine | 2 |
| Sorbitol | 2.5 |
| Gum Arabic | 2 |
| Guar gum | 0.5 |
| TG | 0.2 |
| Konjac mannan | 0.2 |
| NaCl | 1 |
| Phospholipids | 1 |
| Water | 70.6 |

The results as set forth in Table 24 show that addition of phospholipids provided shampoo with good foam stability and after feel, and improved wetting of hair.

TABLE 24

| Shampoo properties | | | | | |
|---|---|---|---|---|---|
| | Body | Smooth On hair | Smooth On hand | Foam stability | After feel |
| Without Phospholipids | 4 | 3 | 3-4 | 4 | 4 |
| With Phospholipids | 3-4 | 4 | 3-4 | 4-5 | 4 |

The formulation of the present example has also been prepared with Aspen bark extract.

Example 14: Formulations Comprising Oils Such as Jojoba Oil

The effect of jojoba oil on performance was tested in the following shampoo formulation (Table 25). The preparation of the shampoo is as previously described.

TABLE 25

| Shampoo composition | |
|---|---|
| Concentration | (% wt) |
| Extract of Sapindus Mukorossi | 20 |
| Betaine | 2 |
| Sorbitol | 2.5 |
| Gum Arabic | 2 |
| Guar gum | 0.5 |
| TG | 0.2 |
| Konjac mannan powder food | 0.2 |
| NaCl | 1 |
| Jojoba oil | 0.3 |
| Water | 70.6 |

The results as set forth in Table 26 show that addition of Jojoba oil provided a shampoo with good smoothness and after feel. It should be noted that although it is known that oils interfere with foaming, surprisingly the jojoba oil did not cause a significant deterioration in the foam properties, while providing an improvement in the after feel and smooth feeling during application.

TABLE 26

| Shampoo properties | | | | |
|---|---|---|---|---|
| | Body | Smooth On hand | Foam stability | After feel |
| Without oil | 4 | 3-4 | 4 | 4 |
| With oil | 3-4 | 4-5 | 3-4 | 4-5 |

Example 15: Shampoos with Rhamnolipids

The following shampoo formulations were prepared and tested on 5 babies' heads as a used in commercial shampoo.

TABLE 27

| Shampoo composition | | | | |
|---|---|---|---|---|
| | Concentration (% wt) | | | |
| Composition | Exp. 1 | Exp. 2 | Exp. 3 | Exp. 4 |
| an aqueous-ethanolic extract of Sapindus Mukorossi | 15 | 15 | 20 | 20 |
| an aqueous-ethanolic extract of Camellia oleifera | 5 | 5 | 0 | 0 |
| Betaine | 4 | 4 | 4 | 4 |
| Sorbitol | 5 | 5 | 5 | 5 |
| Gum Arabic | 2 | 1 | 1 | 1 |
| Konjac mannan | 0.2 | 0 | 0.2 | 0.30 |
| Guar gum | 0.375 | 0 | 0.375 | 0 |
| TG | 0.2 | 0 | 0.2 | 0 |
| Xanthan gum | 0 | 0.3 | 0 | 0 |
| Alga gel | 0 | 0.3 | 0 | 0.3 |
| NaCl | 1 | 1 | 1 | 1 |
| Rhamnolipids | 1 | 2 | 2 | 1 |
| Phospholipids | 1 | 0 | 0 | 2 |
| Jojoba oil | 0.1 | 0 | 0 | 0.5 |
| Preservative | 1 | 1 | 1 | 1 |
| Perfume | 1 | 1 | 1 | 1 |
| Water | 63.12 | 64.4 | 64.22 | 62.9 |

The addition Rhamnolipids, a biosurfactant, dramatically improved the wetting on hair. Further, hair and hands washed with the above four compositions of cleaning formulations showed excellent cleaning, foaming and good shine and it was easy to comb the hair after shampooing.

Example 16: Haemolysis Test

Haemolysis test (which serves as a model for eye irritation) was conducted in order to determine the safety of the products of the invention in comparison to the commercial surfactant SLES (sodium lauryl ether sulfate).

Preparation of the Erythrocyte Suspension:

erythrocytes of sheep blood were separated by centrifugation at 1250 g, for 15 minutes at room temperature, washed three times with phosphate-buffered saline solution (PBS, pH 7.4), and centrifuged twice under the same condition. The blood volume was completed with PBS. This suspension was maintained at 4° C. for up to three days.

The Assay Procedure:

20 μl of each sample were diluted up to 2 ml of the suspension, and were incubated with for 30 minutes in ice. The incubation was terminated by a rapid, high-speed (1800 g) centrifugation for 30 minutes. The extent of haemolysis was determined in spectrophotometrically at 540 nm against a blank (PBS). The extent of haemolysis, expressed as a percentage, was calculated as the absorbance of an erythrocyte suspension incubated with each product, relative to that of a completely haemolysed control (100%, at distilled water) at 540 nm. The Hm50 (50% haemolysis) was determined from concentration—response curves.

TABLE 28

Hm$_{50}$ of Sapindus extract and SLES

| | Hm$_{50}$ |
|---|---|
| SLES | 0.001 gram/100 ml |
| Sapindus Mukorossi extract | 1 gram/100 ml |

As can be seen from Table 28, the *Sapindus Mukorossi* extract (extracted by 50 wt % ethanol and 50 wt % water, 60° C., for 6 hours, as described in Example 1), demonstrated a higher potential (×1000) as a non-irritant natural surfactant, causing less damage to the cells in comparison to SLES which was and still is used in many commercial cleansing formulations.

Example 17: Synergistic Effect in Challenge Test

The tests were conducted by adding to a sterile solution an inoculum of a suitable microorganisms as described below and storing the solution at 37° C. for the bacteria or 30° C. for the yeast. Saponin extracted by water/ethanol mixture (50:50) was added at various concentrations as detailed below to a natural preservative cocktail (containing *Wasabia Japonica, Populus tremuloides* and *Lonicera Japonica* at a ratio of 1/1/1). Using serial dilutions and plate counts, aliquots were taken during the incubation period for determination of microorganism count.

Media and reagents used: phosphate buffer 100 mM pH=5.5 (sterile), TSYE (30 gl/l tryptic soy broth +5 gr/l yeast extract) was added to solid media 2% agar, PDB (24 g/l potato dextrose broth +0.2 g/l chloramphenicol) was added for solid media 2% agar and diluent which is sterile solution of 0.9% sodium chloride and 0.1% peptone was used where indicated.

The tested organisms were *Salmonella typhimurium* ATCC 14028, *Escherichia coli* EDL933, *Staphylococcus aureus* MRSA strain Newman D2 ATCC 25904 and *Saccharomyces cerevisiae* ATCC 11777. The three bacteria were grown overnight on TSYE in an incubator shaker at 37° C. Yeast cells were grown overnight on PDB in an incubator shaker at 30° C. The media from the overnight cultures was washed twice with the diluent by centrifugation and each one of the organisms was transfer to 5 ml of the phosphate buffer containing different preservatives combinations to yield 105/ml. The test tubes were incubated either at 37° C. for the bacteria or 30° C. for the yeast. Aliquots were taken during the incubation period for determination of microorganism counts. The numbers in Table 28 below are the means of two separate experiments. Each treatment was repeated three times.

TABLE 29

Total count of different microorganisms as a function of the cocktail preservatives and *Sapindus* extract concentrations

| | Preservatives/*Sapindus* extract wt %. | | | | |
|---|---|---|---|---|---|
| Microorganisms | 0/0 | 0.2/0 | 0.2/2 | 0.2/10 | 0.2/20 |
| E. coli | $10^5$ | $5 \times 10^2$ | <10 | <10 | <10 |
| Salmonella | $10^5$ | $5 \times 10^4$ | $2 \times 10^3$ | <10 | <10 |
| Staphylococcus | $10^5$ | $10^4$ | $10^4$ | $10^4$ | <200 |
| Saccharomyces | $10^5$ | $10^5$ | $10^3$ | 200 | 200 |

TABLE 29-continued

Total count of different microorganisms as a function of the cocktail preservatives and *Sapindus* extract concentrations

| Microorganisms | 0/0 | 0/20 | 0.01/20 | 0.05/20 | 0.1/20 |
|---|---|---|---|---|---|
| E. coli | $10^5$ | $10^5$ | $10^5$ | <10 | <10 |
| Salmonella | $10^5$ | $10^6$ | $10^6$ | $10^3$ | <10 |
| Staphylococcus | $10^5$ | <200 | <200 | <200 | <200 |
| Saccharomyces | $10^5$ | $10^3$ | $10^3$ | 200 | 200 |

As can be seen from Table 29, the preservative cocktail alone or the *Sapindus Mukorossi* extract alone, did not reduce the total microorganisms count below 1000. Only the combination of the preservative cocktail with the *Sapindus Mukorossi* extract caused the total microorganisms count to drop below 10. These surprising results indicate a synergistic effect between the saponin material, e.g., *Sapindus Mukorossi* extract and the preservative cocktail.

Further experiments were conducted under the same conditions with an extract of saponin together with each of *Wasabia Japonica, Populus tremuloides* and *Lonicera Japonica* extracts. Other experiments were conducted with an extract of saponin together with *Wasabia Japonica* and *Populus tremuloides*. Further experiments were conducted with saponin extract together with *Populus tremuloides* and *Lonicera Japonica* extracts. Yet additional experiments were conducted with saponin extract together with *Wasabia Japonica* and *Lonicera Japonica* extracts.

Example 18: Liquid Shampoo

The following shampoo formulations were prepared and tested on hair tresses in the laboratory. The procedure tested was determined according to "Standard guide for descriptive analysis of shampoo performance" (ASTM international, designation: E2082-06). The compositions of the shampoos were determined by "design of experiment".

Application and Foam Characteristics

Test Procedure: Tress was placed in glass warm water (40 to 50° C.) and wetted. After then, the water was drained. 1 ml (1 g) of product was applied onto the wet hair tress, and hair was being shampooing. The ease of spreading, speed of foam, amount of foam, cushion of foam, bubble size, and wetness of foam were evaluated.

Testing Parameters Scale:

Ease of spreading, ease of distributing the product evenly over the surface of the hair prior to generating the foam, from not easy difficult—0 to easy—10

Speed to foam, measure of the time or degree of manipulation required to generate foam, seconds Amount of foam, assessment of the volume of foam after each of several points from none—0 to high—10

Cushion of foam, measure of the force to compress the foam between the thumb and forefinger from none—0 to high—10

Wetness of foam, amount of moisture perceived in the foam mass from dry—0 to wet—10

Bubble size, visual size of the majority of bubbles small—1 and large—0)

Ease of rinsing, time to rinse product out of tress, second

Wet Hair Characteristics

Test Procedure: After washing, the hair tress was combed from the top of the hair tress down to the end of the tress. The ease of detangling and force to comb were evaluated.

The wet feel/slipperiness and residue were evaluated by holding wet hair tress loosely in a closed fist, and rubbing hair between thumb and index finger in a downward motion.

Testing Parameters Scale:

Ease of detangling, ease of removing the tangles from the hair tress from not easy/difficult—0 to easy—10

Force to comb, force applied to the comb to move it through the hair tress, Apply and measure only the minimum and necessary force, from high—0 to none—10

Wet feel/Slipperiness, presence or absence of resistance when moving the fingers down the hair between the thumb and forefinger from drag—0 to slits—10

Residue (greasy/oily/waxy), total amount of all residues left on hair (tactile sensation). The individual types of residues may be identified and quantified, from none—0 to high—10

Dry Hair Characteristics

Test Procedure: The tress was dried by hanging in a hood dryer or using a hand-held blow dryer. The same drying procedure should be used by each evaluator, Evaluate for ease of detangling and force to comb were done by Combing the hair tress from the top and moving down. The dry feel/slipperiness, residue and pliability were evaluated by holding the dry tress loosely in a closed fist, and rubbed hair between thumb and index finger in a downward motion. Continue to comb in a vigorous manner in order to evaluate the electrostatic of the hair.

Testing Parameters Scale:

Ease of detangling, ease of removing the tangles from the hair tress from not easy/difficult—0 to easy—10

Force to comb, force applied to the comb to move it through the hair tress, Apply and measure only the minimum and necessary force, from high—0 to none—10)

However, the hair is evaluated in sections (for example, middle section, ends).

Dry feel/slipperiness, presence or absence of resistance when moving the fingers down the hair between the thumb and forefinger from drag—0 to slip—10

Residue, total amount of all residues left on hair (tactile sensation). The individual types of residues may be identified and quantified, from none—0 to high—10

Pliability, measure of the force required to bend the hair, not stiff or rigid from low—10 to high—0

Static, degree that the individual hair shafts repel each other from none—10 to high—10

The Effect of Polysaccharides and Humectants

The effect of polysaccharides and humectants (sorbitol) and saponins were tested in the following shampoo formulations. The preparation of the shampoo was performed according to Example 4.

TABLE 30

Shampoo compositions with saponins, polysaccharides and humectants

| INCI name | Natural source | Concentration (wt %) | | |
|---|---|---|---|---|
| | | #1 | #2 | #3 |
| Sapindus mukurossi fruit extract | Sapindus extract | 6.00 | 2.50 | 2.50 |
| Camellia oleifera seed extract | Camellia extract/tea extract | — | 5.00 | — |
| Saponaria officinalis root extract | Saponaria extract | — | — | 2.00 |
| Ramnolipids | P. aeruginosa extract | — | 1.00 | — |
| Sorbitol | Fruit extract | 14.00 | 14.00 | — |
| Xanthan gum | Xanthomonas fermentation | 0.10 | 0.10 | 0.10 |
| Konjac gum | Konjac extract | 0.10 | 0.10 | 0.10 |
| Lecithin | Soy extract | 3.00 | 3.00 | 3.00 |
| Natural fragrance | Plants extract | 0.30 | 0.30 | 0.30 |
| Aspen bark extract | Aspen bark extract | 0.70 | 0.70 | 0.70 |
| Water | | 55.80 | 60.30 | 85.80 |

Testing Results:

The testing results of the three shampoo compositions nos. 1 to 3 (as detailed in Table 30) are presented in Table 31, below.

TABLE 31

Properties of Shampoo compositions nos. 1 to 3 according to Table 30

| Property | Shampoo Composition | | |
|---|---|---|---|
| | #1 | #2 | #3 |
| Ease of spreading | 4 | 8 | 3 |
| Speed of Foam | 6 | 1 | 10 |
| Amount of Foam | 6 | 8 | 2 |
| Cushion of Foam | 4 | 9 | 0 |
| Wetness of foam | 4 | 5 | 0 |
| Bubble size | 1 | 1 | 1 |
| Ease of rinsing | 2 | 2 | 2 |

The testing results demonstrate that saponins, polysaccharides, humectant can serve as a good shampoo with high amount of foam, satisfied cushion and wetness of foam, with small bubbles size (#1 and 2). When sorbitol is not included in the composition, the amount, cushion, and the wetness of foam are inferior. Additions of tea extract increases the amount of the foam significantly.

Example 20: The Effect of Different Oils on the Shampoo Performance

The effect of different oils on performance was tested in the following shampoo formulations (Table 32). The preparation of the shampoo is as previously described

TABLE 32

Compositions of liquid shampoo with saponins, polysaccharides, humectant and different oils (oily moisturization)

| INCI name | Natural source | Concentration (wt %) | | | | | |
|---|---|---|---|---|---|---|---|
| | | #1 | #2 | #3 | #4 | #5 | #6 |
| Sapindus mukurossi fruit extract | Sapindus extract | 9.00 | 9.00 | 9.00 | 9.00 | 9.00 | 9.00 |

TABLE 32-continued

Compositions of liquid shampoo with saponins, polysaccharides, humectant and different oils (oily moisturization)

| INCI name | Natural source | Concentration (wt %) | | | | | |
|---|---|---|---|---|---|---|---|
| | | #1 | #2 | #3 | #4 | #5 | #6 |
| *Camellia oleifera* seed extract | *Camellia* extract | 5.00 | 5.00 | 5.00 | 5.00 | 5.00 | 5.00 |
| Glycerin | Vegetable glycerin | 10.00 | 10.00 | 10.00 | 10.00 | 10.00 | 10.00 |
| Xanthan gum | *Xanthomonas* fermentation | 0.10 | 0.10 | 0.10 | 0.10 | 0.10 | 0.10 |
| Betaine | Sugar beet extract | 4.00 | 4.00 | 4.00 | 4.00 | 4.00 | 4.00 |
| Lecithin | Soy extract | 3.00 | 3.00 | 3.00 | 3.00 | 3.00 | 3.00 |
| Aspen bark extract | Aspen bark extract | 0.70 | 0.70 | 0.70 | 0.70 | 0.70 | 0.70 |
| Natural Fragrance | Plants extract | 0.30 | 0.30 | 0.30 | 0.30 | 0.30 | 0.30 |
| Almond oil | Almond plant | — | 2.00 | — | — | — | — |
| Jojoba oil | Jojoba plant | — | — | 2.00 | 2.00 | 2.00 | 2.00 |
| Squalene | Olive oil extract | — | — | — | 1.00 | — | 1.00 |
| Lanolin | Extract from wool | — | — | 2.00 | 2.00 | — | — |
| water | | 75.90 | 73.90 | 71.90 | 62.90 | 65.90 | 72.90 |

Testing results: the testing results of the six shampoo compositions nos. 1 to 6 (as detailed in Table 32) are presented in Table 33 below.

TABLE 33

Shampoo properties of the shampoo compositions nos. 1 to 6 as detailed in Table 30

| | #1 | #2 | #3 | #4 | #5 | #6 |
|---|---|---|---|---|---|---|
| Ease of spreading | 8 | 7 | 6 | 8 | 8 | 8 |
| Speed to foam, sec | 5 | 3 | 0 | 10 | 2 | 3 |
| Amount of foam | 7 | 9 | 0 | 4 | 9 | 9 |
| Cushion of foam | 5 | 8 | 0 | 0 | 8 | 8 |
| Wetness of foam | 4 | 8 | 0 | 0 | 7 | 7 |
| Bubble size | 1 | 1 | 0 | 0 | 1 | 1 |
| Ease of rinsing, sec | 2 | 2 | 0 | 2 | 2 | 2 |

The results as set forth in Table 33 show that addition of lanolin reduced significantly the foaming of the formula (#3 and 4) compared to formula #1. However, addition of almond oil (#2), and even more, addition of jojoba oil (#5) or combination of jojoba oil/squalene (#6) increased the amount of foam, the cushion and the wetness compared to formula without oil (#1).

Example 21: The Effect of Humectants (Betaine, Sorbitol, Glycerol, Honey) on the Shampoo Performance

TABLE 34

Compositions of liquid shampoo with saponins, polysaccharides, oil and different humectants

| INCI name | Natural source | Concentration (wt %) | | | | | | |
|---|---|---|---|---|---|---|---|---|
| | | #1 | #2 | #3 | #4 | #5 | #6 | #7 |
| *Sapindus mukorossi* fruit extract | *Sapindus* extract | 9.0 | 9.0 | 9.0 | 9.0 | 9.0 | 9.0 | 9.0 |
| *Camellia oleifera* seed extract | *Camellia* extract | 5.0 | 5.0 | 5.0 | 5.0 | 5.0 | 5.0 | 5.0 |
| Carrageenan | Seaweeds extract | 0.5 | 0.5 | 0.5 | 0.5 | 0.5 | 0.5 | 0.5 |
| Veegum | Natural clay | 3.0 | 3.0 | 3.0 | 3.0 | 3.0 | 3.0 | 3.0 |
| Colloidal oatmeal | Oatmeal extract | 0.5 | 0.5 | 0.5 | 0.5 | 0.5 | 0.5 | 0.5 |
| Lecithin | Soy extract | 3.0 | 3.0 | 3.0 | 3.0 | 3.0 | 3.0 | 3.0 |
| Aspen bark extract | Aspen bark extract | 0.7 | 0.7 | 0.7 | 0.7 | 0.7 | 0.7 | 0.7 |
| Natural fragrance | Plants extract | 0.3 | 0.3 | 0.3 | 0.3 | 0.3 | 0.3 | 0.3 |
| Jojoba oil | Jojoba extract | 1.0 | 1.0 | 1.0 | 1.0 | 1.0 | 1.0 | 1.0 |
| Squalene | Olive oil extract | 1.0 | 1.0 | 1.0 | 1.0 | 1.0 | 1.0 | 1.0 |
| Betaine | Sugar beet extract | — | 2.0 | 2.0 | 2.0 | 2.0 | 2.0 | 2.0 |
| Glycerin | Vegetable glycerin | — | 1.5 | 0.5 | 0.5 | 2.5 | 0.5 | 2.5 |
| Sorbitol | Fruit extract | — | — | 0.7 | 1.4 | 1.4 | — | — |
| Honey | Honey extract | — | 0.5 | — | — | — | 1.0 | 0.5 |
| Water | | 72.5 | 72.5 | 73.5 | 73.5 | 71.5 | 73.5 | 71.5 |

The effect of humectants on performance was tested in the following shampoo formulations (Table 34). The preparation of the shampoo is as previously described.

Testing results: the testing results of the seven shampoo compositions nos. 1 to 7 (as detailed in Table 34) are presented in Table 35 below.

TABLE 35

Properties of the shampoo compositions as detailed in Table 32

|  | #1 | #2 | #3 | #4 | #5 | #6 | #7 |
|---|---|---|---|---|---|---|---|
| Application and Foam Characteristics | | | | | | | |
| Ease of spreading | 7 | 8 | 8 | 8 | 8 | 8 | 7 |
| Speed to foam, sec | 5 | 4 | 5 | 10 | 10 | 6 | 10 |
| Amount of foam | 7 | 9 | 9 | 8 | 7 | 8 | 6 |
| Cushion of foam | 5 | 5 | 7 | 8 | 5 | 8 | 5 |
| Wetness of foam | 5 | 6 | 7 | 6 | 5 | 7 | 5 |
| Bubble size | 1 | 1 | 1 | 1 | 1 | 1 | 1 |
| Ease of rinsing, sec | 2 | 2 | 2 | 2 | 2 | 2 | 2 |

TABLE 35-continued

Properties of the shampoo compositions as detailed in Table 32

|  | #1 | #2 | #3 | #4 | #5 | #6 | #7 |
|---|---|---|---|---|---|---|---|
| Wet flair Characteristics | | | | | | | |
| Ease of detangling | 8 | 8 | 7 | 7 | 7 | 6 | 5 |
| Force to comb | 8 | 8 | 8 | 8 | 7 | 7 | 5 |
| Wet feel/Slipperiness | 9 | 9 | 9 | 8 | 9 | 9 | 8 |
| Residue (greasy/oily/waxy) | 9 | 9 | 9 | 9 | 9 | 9 | 7 |
| Dry Hair Characteristics | | | | | | | |
| Ease of detangling | 8 | 8 | 8 | 8 | 9 | 6 | 7 |
| Force to comb | 9 | 9 | 9 | 9 | 9 | 7 | 8 |
| Dry feel/Slipperiness | 9 | 9 | 9 | 9 | 9 | 9 | 9 |
| Residue (greasy/oily/waxy) | 9 | 9 | 9 | 9 | 9 | 9 | 9 |
| Pliability | 9 | 9 | 9 | 9 | 9 | 9 | 9 |
| Static | 7 | 7 | 7 | 7 | 8 | 8 | 7 |

The testing results as set forth in Table 35 show, that addition of most of the humectants types and concentrations were increased the amount of the foam and the ease of spreading (expect #7) compared to formula #1. The best cushion and wetness of foam were obtained when the humectants glycerol/sorbitol were at weight ratio of 0.5/0.7 (#3), 0.5/1.4 (#4) and glycerin/honey 0.1/1 (#6). On Wet Hair, most of the humectants decreased slightly the ease of detangling. No significant changes were observed on dry Hair.

Example 22: The Effect of Moisturization (Non-Oily) Materials and Clays

The effect of moisturization materials on performance was tested in the following shampoo formulations (Table 36). The preparation of the shampoo is as previously described.

TABLE 36

Compositions of liquid shampoo with saponins, polysaccharides, humectant, oils and moisturization materials

| | | Concentration (wt %) | | | | | |
|---|---|---|---|---|---|---|---|
| INCI name | Natural source | #1 | #2 | #3 | #4 | #5 | #6 |
| *Sapindus mukurossi* fruit extract | *Sapindus* extract | 9.00 | 9.00 | 9.00 | 9.00 | 9.00 | 9.00 |
| *Camellia oleifera* seed extract | *Camellia* extract | 5.00 | 5.00 | 5.00 | 5.00 | 5.00 | 5.00 |
| Glycerin | Vegetable glycerin | 1.70 | 1.70 | 1.70 | 1.70 | 1.70 | 1.70 |
| Sorbitol | Fruit extract | 0.70 | 0.70 | 0.70 | 0.70 | 0.70 | 0.70 |
| Betaine | Sugar beet extract | 2.00 | 2.00 | 2.00 | 2.00 | 2.00 | 2.00 |
| Carrageenan | Seaweeds extract | 0.50 | 0.50 | 0.50 | 0.50 | 0.50 | 0.50 |
| Aspen bark extract | Aspen bark extract | 0.70 | 0.70 | 0.70 | 0.70 | 0.70 | 0.70 |
| Natural fragrance | Plants extract | 0.30 | 0.30 | 0.30 | 0.30 | 0.30 | 0.30 |
| Jojoba oil | Jojoba extract | 1.00 | 1.00 | 1.00 | 1.00 | 1.00 | 1.00 |
| Squalene | Olive oil extract | 1.00 | 1.00 | 1.00 | 1.00 | 1.00 | 1.00 |
| Lechitin | Soy extract | — | — | — | — | — | — |
| *Aloe Barbadensis* Leaf Juice | *Aloe Barbadensis* Leaf Juice | — | — | — | — | — | 2.0 |
| Urea | | — | 2.00 | — | — | — | — |
| Colloidal oatmeal | Oat meal extract | — | — | 0.5 | — | — | 0.5 |
| Veegum | Natural clay | — | — | — | 1.00 | — | 0.6 |
| Bentonite | Natural clay | — | — | — | — | 1.00 | — |
| water | | 78.1 | 76.1 | 77.6 | 77.1 | 77.1 | 77.8 |

Testing results: the testing results of the six shampoo compositions nos. 1 to 6 (as detailed in Table 36) are presented in Table 37 below.

TABLE 37

Shampoo properties

|  | #1 | #2 | #3 | #4 | #5 | #6 |
|---|---|---|---|---|---|---|
| Application and Foam Characteristics | | | | | | |
| Ease of spreading | 7 | 8 | 8 | 8 | 8 | 9 |
| Speed to foam, sec | 5 | 4 | 4 | 4 | 5 | 3 |
| Amount of foam | 7 | 9 | 9 | 9 | 9 | 9 |
| Cushion of foam | 5 | 9 | 9 | 7 | 9 | 9 |
| Wetness of foam | 4 | 9 | 7 | 7 | 9 | 8 |
| Bubble size | 1 | 1 | 1 | 1 | 1 | 1 |
| Ease of rinsing, sec | 2 | 2 | 2 | 2 | 2 | 2 |
| Wet Hair Characteristics | | | | | | |
| Ease of detangling | 8 | 8 | 4 | 5 | 8 | 8 |
| Force to comb | 8 | 8 | 5 | 6 | 8 | 8 |

TABLE 37-continued

Shampoo properties

|  | #1 | #2 | #3 | #4 | #5 | #6 |
|---|---|---|---|---|---|---|
| Wet feel/Slipperiness | 8 | 9 | 8 | 7 | 9 | 9 |
| Residue (greasy/oily/waxy) | 9 | 9 | 9 | 9 | 9 | 9 |
| Dry Hair Characteristics | | | | | | |
| Ease of detangling | 9 | 9 | 8 | 8 | 9 | 9 |
| Force to comb | 9 | 9 | 9 | 8 | 9 | 9 |
| Dry feel/Slipperiness | 9 | 9 | 9 | 8 | 9 | 9 |
| Residue (greasy/oily/waxy) | 9 | 9 | 9 | 9 | 9 | 9 |
| Pliability | 9 | 9 | 9 | 9 | 9 | 9 |
| Static | 8 | 9 | 7 | 6 | 7 | 7 |

The results as set forth in Table 37 show that addition of moisturization materials increases the amount of the foam, cushion and wetness (#2 and 3) compared to formula #1. Decreased in wet hair characteristics were observed in shampoo that contains colloidal oatmeal. Addition of clays attributed to amount of foam the cushion and wetness (#4 and 5). Addition of Aloe vera gel, Colloidal oatmeal, Veegum and Lecithin improved significantly the shampoo performance compared to formula without them (#1).

Example 23: Liquid Shampoos

The following shampoo formulations were prepared and tested on 5 babies.

TABLE 38

Shampoo compositions

| INCI name | Natural source | #1 | #2 | #3 | #4 |
|---|---|---|---|---|---|
| *Sapindus mukurossi* fruit extract | *Sapindus* extract | 9.00 | 10.00 | 9.00 | 6.0 |
| *Camellia oleifera* seed extract | *Camellia* extract | 5.00 | — | 5.00 | 1.5 |
| *Saponaria officinalis* root extract | *Saponaria* extract | — | 10.0 | — | — |
| Rhamnolipids | *P. aeruginosa* extract | — | — | — | 4.0 |
| Honey | Honey extract | 0.50 | — | 0.50 | — |
| Sorbitol | Fruit extract | — | 1.7 | — | 10.0 |
| Glycerol | Vegetable glycerin | — | 0.7 | — | — |
| Lactic acid | Milk acid | 1.00 | — | 1.00 | — |
| Betaine | Sugar beet extract | 2.00 | 2.00 | 2.00 | — |
| Taurocholate | Bile salt | — | — | 0.60 | — |
| *Aloe Barbadensis* Leaf Juice | *Aloe Barbadensis* Leaf Juice | 2.00 | — | 2.00 | — |
| Carrageenan | Seaweeds extract | 0.50 | 0.3 | 0.50 | 0.25 |
| Xanthan gum | Xanthomonas fermentation | 0.00 | 0.2 | 0.00 | 0.20 |
| Veegum | Natural Clay | 0.60 | 3 | 0.60 | 2.50 |
| Lecithin | Soy extract | 3.00 | 3 | 3.00 | 3.00 |
| Colloidal oatmeal | Oatmeal extract | 0.50 | 0.5 | 0.50 | — |
| Natural fragrance | Plants extract | 0.30 | 0.3 | 0.30 | 0.30 |
| Aspen bark extract | Aspen bark extract | 0.70 | 0.7 | 0.70 | 0.70 |
| Jojoba oil | Jojoba plant | 1.00 | 1.00 | 1.00 | — |
| Squalene | Olive oil extract | 1.00 | 1.00 | 1.00 | — |
| water | | 73.9 | 66 | 73.3 | 71.50 |

Babies' hair washed with all of the above shampoos, showed excellent cleaning performance, foaming, good shine and it was easy to comb dry hair after shampooing.

Example 24: Facial Cleansing

The following facial cleansing formulations in according to the invention were prepared as detailed in Table 39. These formulations showed excellent facial cleansing performance, with pleasant after feel.

TABLE 39

Facial cleansing toner for oily skin and dry skin and Facial milk formulation according to the invention

| | Toner | | Facial |
|---|---|---|---|
| | oily skin | dry skin | Cleansing |
| | Concentration (wt %) | | |
| *Sapindus* extract | 3.00 | 2.00 | 2.00 |
| Ethanol | 3.50 | — | — |
| Sorbitol | — | 10.00 | 8.50 |
| Carrageenan | 0.20 | 0.20 | 0.30 |
| Xanthan Gum | — | — | 0.30 |
| Veegum | — | — | 1.50 |
| Betaine | 3.00 | 3.00 | — |
| Aspen bark extract | 0.70 | 0.70 | 0.70 |
| Natural Fragrance | 0.30 | 0.30 | 0.30 |
| Jojoba oil | — | — | 10.00 |
| Water | 89.30 | 83.80 | 76.90 |

Example 25: Facial Cream

The following face cream formulations in according to the invention were prepared as detailed in Table 40.

TABLE 40

Face cream formulations according to the invention

| | Concentration (wt %) | |
|---|---|---|
| | #1 | #2 |
| *Sapindus* extract | 2.50 | 2.50 |
| Xanthan Gum | 0.20 | 0.35 |
| Carrageenan | 0.20 | 0.35 |
| Veegum | 2.00 | 0.00 |
| Aspen bark extract | 0.70 | 0.70 |
| Sorbitol | 5.00 | 5.00 |
| Shea Butter | 10.00 | 10.00 |
| Jojoba oil | 10.00 | 10.00 |
| Almond oil | 10.00 | 14.00 |
| Lecithin | 1.50 | 1.50 |
| Candelilla wax | — | 3.00 |
| Beeswax | 1.50 | 1.50 |
| Rice Starch | 1.00 | 1.00 |
| Water | 55.40 | 50.10 |

The invention claimed is:
1. A personal-care foaming composition, comprising:
   a naturally-obtained saponin material present in an amount ranging from 5 to 20 wt %, wherein the saponin material comprises an extract from *Sapindus mukorossi*;
   at least one naturally-obtained thickening agent selected from the group consisting of Xanthan gum, Carrageenan gum, Konjac gum, Veegum, bentoine, gum Arabic, Guar gum, and starch;
   at least one naturally-obtained humectant selected from the group consisting of betaine, natural urea, lactic acid, colloidal oat meal, glycerin, sorbitol, mannitol, honey, Aloe vera, shea butter, and hyaluronic acid;
   an effective amount of at least one naturally-obtained preservative being a *Populus* extract, a *Lonicera* extract, *Wasabia* extract, and *Salix* extract; and
   at least one naturally-obtained additive selected from the group consisting of lecithin, egg-yolk oil, tocopherol (vitamin E), a phospholipid, almond oil, jojoba oil, squalene, lanoline, taurocholate, candelilla wax, bees wax, and any combination thereof.

2. The composition according to claim 1, wherein the saponin-material is provided in the form of an extract, the extract comprising between 0.2% and 95 wt % saponins out of the total weight of the dry content of the extract.

3. The composition according to claim 1, wherein the saponin material is obtained by extraction from a plant source, said extraction process being carried out by water, alcohol or a water/alcohol solution.

4. The composition according to claim 3, wherein the water/alcohol solution has a water:alcohol ratio of from 80:20 to 20:80 or from 60:40 to 40:60 or from 70:30 to 30:70 or is of a ratio 50:50.

5. The composition according to claim 1, wherein the saponin material is extracted from a plant source following a method comprising:
   1. treating the plant source in a water:alcohol solution having a water:alcohol ratio of from 40:60 to 60:40 for a period of time and under conditions permitting extraction of the saponin material from said plant source into said solution;
   2. optionally drying said saponin-containing solution to obtain a saponin-containing solid material; and
   3. optionally, purifying said saponin-containing solid material.

6. The composition according to claim 1, comprising at least one natural surfactant or bio-surfactant.

7. The composition according to claim 6, wherein the at least one natural surfactant is a phospholipid.

8. The composition according to claim 1, further comprising at least one naturally-obtained moisturizer.

9. The composition according to claim 1, further comprising at least one natural additive selected from the group consisting of anti-irritation plant extracts and amongst anti-oxidation plant extracts.

10. The composition according to claim 1, wherein the naturally-obtained preservative material comprises a *Lonicera* extract as an extract of *Lonicera japonica*, a *Populus* extract as an extract of *Populus tremuloides*, a *Wasabia* extract as an extract of *Wasabia japonica* and a *Salix* extract as an extract of *Salix alba*.

11. The composition according to claim 1, the composition being selected from the group consisting of a shampoo, a conditioning shampoo, a hair conditioner, a moisturizing cream, a deodorant, soap, a liquid soap, a body wash, a moisturizing body wash, a shower gel, a skin cleanser, a cleansing milk, hair care cream or soap, intimate wash, a makeup remover, hair and body wash, in shower body moisturizer, a pet shampoo, a shaving preparation, a shaving foam, a toothpaste, and a mouthwash.

\* \* \* \* \*

UNITED STATES PATENT AND TRADEMARK OFFICE
CERTIFICATE OF CORRECTION

PATENT NO. : 10,064,881 B2
APPLICATION NO. : 13/992309
DATED : September 4, 2018
INVENTOR(S) : Tova Silberstein et al.

It is certified that error appears in the above-identified patent and that said Letters Patent is hereby corrected as shown below:

On the Title Page

Item (73):
Please delete "Yissum Research Development Company of the Hebrew University of Jerusalem Ltd., Jerusalem (IL)"

Signed and Sealed this
Twenty-sixth Day of February, 2019

Andrei Iancu
*Director of the United States Patent and Trademark Office*